(12) United States Patent
Gill et al.

(10) Patent No.: US 11,771,719 B2
(45) Date of Patent: *Oct. 3, 2023

(54) METHODS AND COMPOSITIONS FOR GENE EDITING IN HEMATOPOIETIC STEM CELLS

(71) Applicant: THE TRUSTEES OF THE UNIVERSITY OF PENNSYLVANIA, Philadelphia, PA (US)

(72) Inventors: Saar Gill, Philadelphia, PA (US); Miriam Kim, Philadelphia, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 634 days.

This patent is subject to a terminal disclaimer.

(21) Appl. No.: 16/721,156

(22) Filed: Dec. 19, 2019

(65) Prior Publication Data

US 2020/0281975 A1 Sep. 10, 2020

Related U.S. Application Data

(63) Continuation of application No. 15/970,605, filed on May 3, 2018, now Pat. No. 10,548,922, which is a continuation of application No. PCT/US2016/060273, filed on Nov. 3, 2016.

(60) Provisional application No. 62/250,561, filed on Nov. 4, 2015.

(51) Int. Cl.
| | |
|---|---|
| *A61K 35/17* | (2015.01) |
| *C12N 15/113* | (2010.01) |
| *A61K 35/28* | (2015.01) |
| *C12N 15/11* | (2006.01) |
| *A61P 35/02* | (2006.01) |
| *C12N 15/63* | (2006.01) |
| *A61K 45/00* | (2006.01) |
| *A61K 48/00* | (2006.01) |
| *C12N 15/10* | (2006.01) |
| *A61K 39/00* | (2006.01) |

(52) U.S. Cl.
CPC ............. *A61K 35/17* (2013.01); *A61K 35/28* (2013.01); *A61K 45/05* (2013.01); *A61K 48/005* (2013.01); *A61P 35/02* (2018.01); *C12N 15/102* (2013.01); *C12N 15/111* (2013.01); *C12N 15/113* (2013.01); *C12N 15/63* (2013.01); *A61K 2039/5156* (2013.01); *A61K 2039/5158* (2013.01); *C12N 2310/20* (2017.05)

(58) Field of Classification Search
None
See application file for complete search history.

(56) References Cited

U.S. PATENT DOCUMENTS

| 10,548,922 B2* | 2/2020 | Gill ..................... A61K 48/005 |
|---|---|---|
| 2010/0172882 A1 | 7/2010 | Glazer et al. |
| 2014/0322212 A1 | 10/2014 | Brogdon et al. |
| 2015/0283178 A1 | 10/2015 | June et al. |

FOREIGN PATENT DOCUMENTS

| JP | 2018531260 | 10/2018 |
|---|---|---|
| WO | 2014059173 A2 | 4/2014 |
| WO | 2014191128 A1 | 12/2014 |
| WO | 2017066760 A1 | 4/2017 |

OTHER PUBLICATIONS

Lax, et al. (1990) "Domain deletion in the extracellular portion of the EGF-receptor reduces ligand binding and impairs cell surface expression", Cell Regulation, 1: 173-88. (Year: 1990).*
Ramakrishna, et al. (2014) "Gene disruption by cell-penetrating peptide-mediated delivery of cas9 protein and guide RNA", Genome Research, 24(6): 1020-27. (Year: 2014).*
Florence Borot et al., "Gene-edited stem cells enable CD33-directed immune therapy for myeloid malignancies", Proceedings of the National Academy of Sciences, (May 28, 2019), vol. 116, pp. 11978-11987, XP055643440.
Cong Le et al., "Multiplex Genome Engineering Using CRISPR/Cas Systems", Science, (Feb. 1, 2013), vol. 339, pp. 819-823, XP055458249.
Mandal , et al., "Efficient Ablation of Genes in Human Hematopoietic Stem and Effector Cells using CRISPR/Cas9.", 2014, Cell Stem Cell 15:643-652.
Eurasian Patent Application No. 201891092—Office Action dated Nov. 27, 2019.
European Patent Application No. 16862941.8—European Search Report dated Mar. 22, 2019.
International Patent Application No. PCT/US16/60273—International Search Report and Written Opinion dated Jan. 24, 2017.
Albeituni , et al., 2013, Cancer Journal 19(6):490-501.
Brinkman-Van Der Linden , et al., "CD33/Siglec-3 Binding Specificity, Expression Pattern, and Consequences of Gene Deletion in Mice.", 2003, Molecular and Cellular Biology 23(12):4199-4206.

(Continued)

*Primary Examiner* — Robert M Kelly
(74) *Attorney, Agent, or Firm* — Saul Ewing, LLP; Kathryn Doyle

(57) ABSTRACT

The present invention relates to compositions and methods of generating modified hematopoietic stem or progenitor cells. One aspect of the invention includes a modified hematopoietic stem or progenitor cell comprising a nucleic acid capable of decreasing expression of an endogenous gene or a portion thereof, wherein the endogenous gene encodes a polypeptide comprising an antigen domain targeted by a chimeric antigen receptor (CAR). Another aspect of the invention includes a method for generating a modified hematopoietic stem or progenitor cell. Also included are methods and pharmaceutical compositions comprising the modified cell for adoptive therapy and treating a condition, such as an autoimmune disease or cancer.

9 Claims, 34 Drawing Sheets

Specification includes a Sequence Listing.

(56) References Cited

OTHER PUBLICATIONS

Doench, et al., "Rational design of highly active sgRNAs for CRISPR-Cas9-mediated gene inactivation.", 2014, Nature Biotechnology 32(12):1262-1267.
Janeway, et al., "Responses to alloantigens and transplant rejection.", Immunobiology: The Immune System in Health and Disease. 5th edition. New York: Garland Science; 2001. Responses to alloantigens and transplant rejection. Available from: https://www.ncbi.nlm.nih.gov/books/NBK27163/.
Kenderian, et al., "CD33 Directed Chimeric Antigen Receptor T Cell Therapy as a Novel Preparative Regimen Prior to Allogeneic Stem Cell Transplantation in Acute Myeloid Leukemia.", 2015, Biology of Blood and Marrow Transplantation 21(2): (Feb. 1, 2015) 2 pages.
Kenderian, et al., "CD33-specific chimeric antigen receptor T cells exhibit potent preclinical activity against human acute myeloid leukemia.", 2015, Leukemia 29:1637-1647.
Kim, et al., "Genetic Inactivation of CD33 Hematopoietic Stem Cells to Enable CAR T Cell Immunotherapy for Acute Myeloid Leukemia.", 2018, Cell 173:1439-53 (35 pages printed, with supplementary material).
O'Hear, et al., "Anti-CD33 chimeric antigen receptor targeting of acute myeloid leukemia.", 2014, Hematologica 100(3):336-344.
Ott De Bruin, et al., "Novel genome-editing tools to model and correct primary immunodeficiencies.", 2015 Frontiers in Immunology 6:250 (pp. 1-11).
Wang, et al., "CRISPR/Cas9 in Genome Editing and Beyond.", 2016 The Annual Review of Biochemistry 85:227-64.

\* cited by examiner

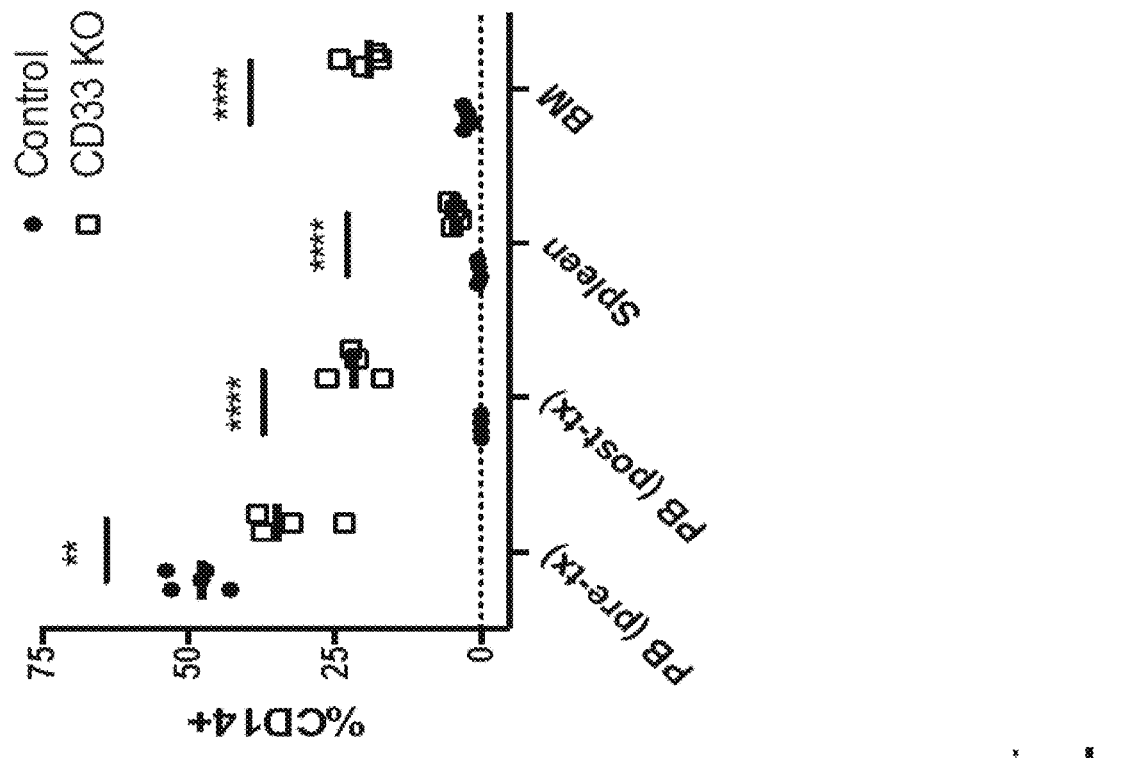
Figure 11D
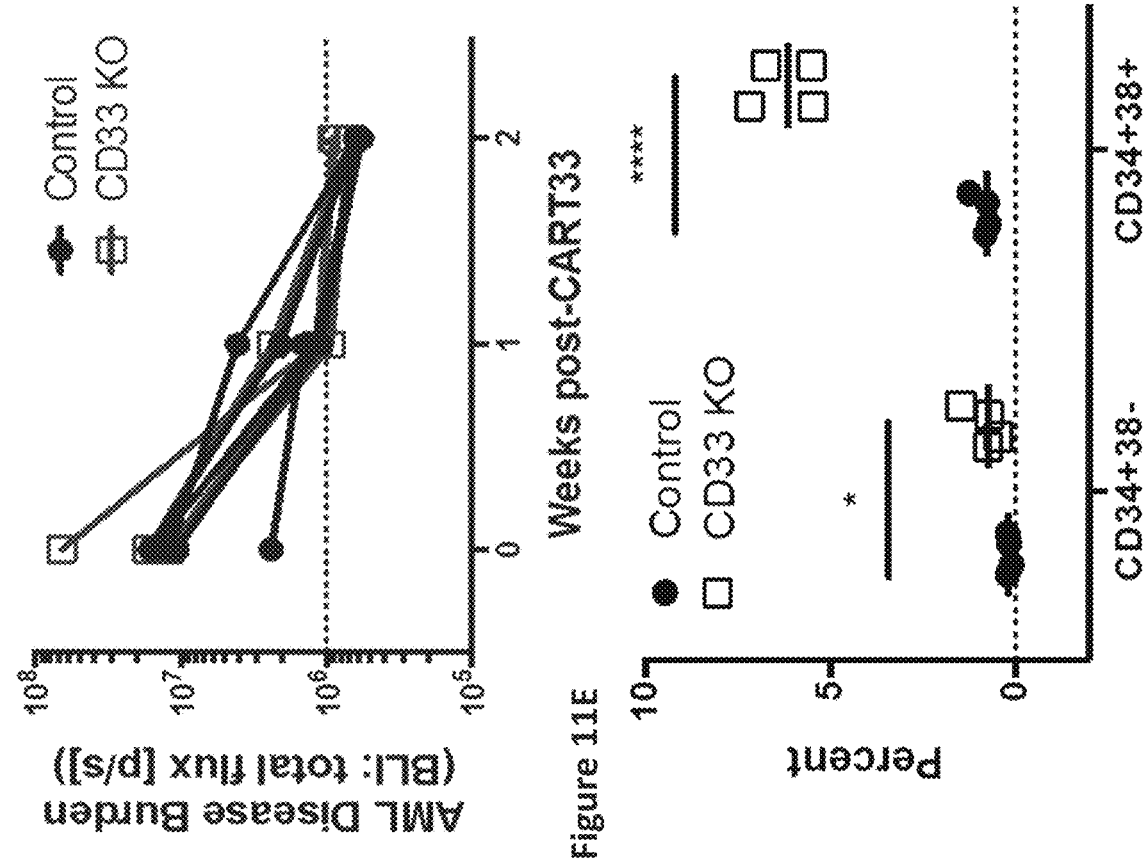
Figure 11C
Figure 11E

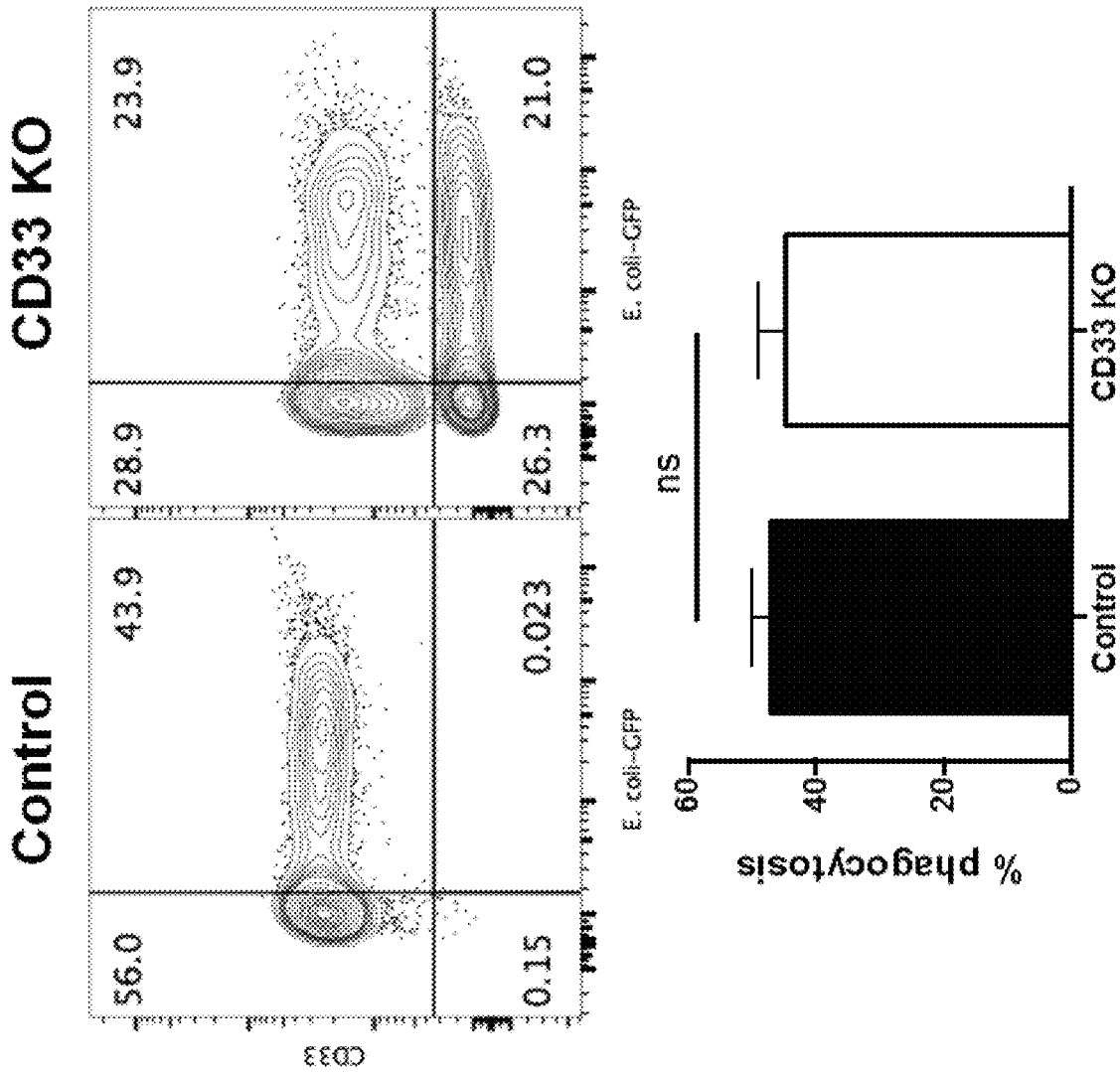

| | Location | #MM | MIT score | CCTop rank | Position |
|---|---|---|---|---|---|
| *CD33* | chr19 | 0 | 100 | 1 | Exon |
| *SIGLEC22P* | chr19 | 0 | 100 | 2 | Exon |
| Chr18 | chr18 | 3 | 1.56 | | Intergenic |
| *ARHGEF10* | | | | | |
| *L* | chr1 | 3 | 1.52 | 3 | Intron |
| *SIGLEC6* | chr19 | 2 | 1.38 | 7 | Exon |
| *SIGLEC17P* | chr19 | 2 | 1.31 | 5 | Exon |
| *GHDC* | chr17 | 4 | 0.77 | 8 | Exon |
| *SIGLEC5* | chr19 | 3 | 0.51 | 8 | Exon |
| *SIGLEC12* | chr19 | 3 | 0.51 | 10 | Exon |
| *SIGLEC14* | chr19 | 3 | 0.51 | 9 | Exon |
| *VMO1* | chr17 | 4 | 0.38 | | Exon |
| Chr2 | chr2 | 3 | 0.29 | 6 | Intergenic |
| Chr1 | chr1 | 3 | 0 | 4 | Intergenic |

MIT (http://crispr.mit.edu/)

CCTop (http://crispr.cos.uni-heidelberg.de/)

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Artificially Synthesized Primer (CD33Forward)

<400> SEQUENCE: 1
agctgcttcc tcagacatgc                                               20

<210> SEQ ID NO 2
<211> LENGTH: 25
<212> TYPE: DNA
<213> ORGANISM: Artificial Sequence
<220> FEATURE:
<223> OTHER INFORMATION: Artificially Synthesized Primer (CD33Reverse)

<400> SEQUENCE: 2
ctgtatttgg tacttcctct ctcca                                         25

<210> SEQ ID NO 3
<211> LENGTH: 20
<212> TYPE: DNA
<213> ORGANISM: Artificial Sequence
<220> FEATURE:
<223> OTHER INFORMATION: CD33 gRNA

<400> SEQUENCE: 3
gagtcagtga cggtacagga                                               20

<210> SEQ ID NO 4
<211> LENGTH: 38
<212> TYPE: DNA
<213> ORGANISM: Artificial Sequence
<220> FEATURE:
<223> OTHER INFORMATION: CD33 gRNA + PAM + overhangs

<400> SEQUENCE: 4
gcaggagtca gtgacggtac aggagggttt gtgcgtcc                           38

<210> SEQ ID NO 5
<211> LENGTH: 39
<212> TYPE: DNA
<213> ORGANISM: Artificial Sequence
<220> FEATURE:
<223> OTHER INFORMATION: ss oligo- HDR repair template

<400> SEQUENCE: 5
gcaggagtca gtgacggtac aaggagggtt tgtgcgtcc                          39

<210> SEQ ID NO 6
<211> LENGTH: 36
<212> TYPE: DNA
<213> ORGANISM: Artificial Sequence
<220> FEATURE:
<223> OTHER INFORMATION: Artificially generated sequence

<400> SEQUENCE: 6
gcaggagtca gtgacggtag agggtttgt gcgtcc                              36

<210> SEQ ID NO 7
<211> LENGTH: 24
<212> TYPE: DNA
<213> ORGANISM: Artificial Sequence

```
<220> FEATURE:
<223> OTHER INFORMATION: Artificially generated sequence

<400> SEQUENCE: 7
gcaggagtca gtgacggtgc gtcc                                          24

<210> SEQ ID NO 8
<211> LENGTH: 23
<212> TYPE: DNA
<213> ORGANISM: Artificial Sequence
<220> FEATURE:
<223> OTHER INFORMATION: Artificially generated sequence

<400> SEQUENCE: 8
gcaggagtca gtgacgtgcg tcc                                           23

<210> SEQ ID NO 9
<211> LENGTH: 19
<212> TYPE: DNA
<213> ORGANISM: Artificial Sequence
<220> FEATURE:
<223> OTHER INFORMATION: Artificially generated sequence

<400> SEQUENCE: 9
gcaggaggtt tgtgcgtcc                                                19

<210> SEQ ID NO 10
<211> LENGTH: 18
<212> TYPE: DNA
<213> ORGANISM: Artificial Sequence
<220> FEATURE:
<223> OTHER INFORMATION: Artificially generated sequence

<400> SEQUENCE: 10
gcaggagtca gtgcgtcc                                                 18
```

METHODS AND COMPOSITIONS FOR GENE EDITING IN HEMATOPOIETIC STEM CELLS

CROSS-REFERENCE TO RELATED APPLICATIONS

The present application is a continuation of U.S. patent application Ser. No. 15/970,605, filed May 3, 2018, issued as U.S. Pat. No. 10,548,922, which is a continuation of PCT/US2016/060273, filed Nov. 3, 2016, which claims priority under 35 U.S.C. § 119(e) to U.S. Provisional Patent Application No. 62/250,561, filed Nov. 4, 2015, each of which applications are incorporated herein by reference in their entireties.

BACKGROUND OF THE INVENTION

Powerful antigen-specific immunotherapies such as chimeric antigen receptor (CAR) T cells (CART cells), antibody-drug conjugates or bispecific T cell engaging antibodies (BITE), represent novel approaches to the treatment of cancer. Increased potency is associated with increased on-target off-tumor toxicity, such as the prolonged B cell aplasia that results from CART19 treatment of B cell malignancies. In essence, this is because none of these modalities are able to discriminate between malignant cells and their normal counterparts that carry the same cell surface antigen. CART cells are a novel therapy in which T cells are genetically engineered to recognize and kill cells expressing a specific antigen on its surface. The CAR is a hybrid of an antigen-recognition domain of an antibody combined with the intracellular signaling domains of a T cell surface receptor. CART cells targeting CD19 have shown efficacy against B-cell malignancies in several phase I clinical trials (Grupp et al, New England Journal of Medicine. 2013; 368: 1509-1518; Brentjens et al, Blood. 2011; 118: 4817-4828; and Kochenderfer et al, Blood. 2010; 116: 4099-4102) and deplete normal B cells. Since protracted B-lymphophenia is well tolerated by humans, this particular toxicity has not been dose-limiting after CART19. However, CART cells targeting acute myeloid leukemia (AML) antigens, such as CD123 or CD33, eradicate leukemia cells and consequently deplete normal myeloid progenitors since these bear the same surface antigens, thus leading to bone marrow aplasia. The absence of surface antigens that are selectively expressed on AML cells and not on normal myeloid cells limits the use of CART cells in AML and other myeloid diseases (which include myelodysplastic and myeloproliferative neoplasms).

Therefore a need exists for selectively targeting tumor cells without depleting normal myeloid progenitors. The present invention satisfies this need.

SUMMARY OF THE INVENTION

The present invention relates to compositions and methods of generating modified hematopoietic stem or progenitor cells.

In one aspect, the invention includes a method of protecting a hematopoietic stem or progenitor cell from a chimeric antigen receptor (CAR) T cell therapy in a subject in need thereof. The method of the invention comprises administering to the subject a modified hematopoietic stem or progenitor cell, wherein the stem or progenitor cell comprises a nucleic acid capable of decreasing expression of an endogenous gene or a portion thereof, wherein the endogenous gene encodes a polypeptide comprising an antigen domain targeted by a CAR. In one embodiment, the method of the invention further comprises administering the CAR T cell therapy to the subject in need thereof. In another embodiment, the modified cell further comprises a modified endogenous gene that encodes a modified polypeptide lacking the antigen domain targeted by the CAR.

In another aspect, the invention includes a method for generating a modified hematopoietic stem or progenitor cell. The method of the invention comprises introducing a nucleic acid capable of decreasing expression of an endogenous gene or a portion thereof into the cell, wherein the endogenous gene encodes a polypeptide comprising an antigen domain targeted by a chimeric antigen receptor (CAR). In one embodiment, the method comprises obtaining the cell from a subject in need of CART cell therapy. In another embodiment, the method further comprises introducing a modified endogenous gene into the modified cell, wherein the modified endogenous gene encodes a modified polypeptide lacking the antigen domain targeted by the CAR.

In one embodiment, the nucleic acid capable of decreasing the endogenous gene expression is a CRISPR system. In one embodiment, the CRISPR system comprises a Cas expression vector and a guide nucleic acid sequence specific for the endogenous gene. In another embodiment, the CRISPR system comprises a Cas9 protein complexed with a guide nucleic acid sequence specific for the endogenous gene. In another embodiment, the CRISPR system comprises an inducible promoter. In a further embodiment, the methods of the invention as described herein further comprise exposing the hematopoietic stem or progenitor cell to an agent that activates the inducible promoter in the Cas expression vector.

In one embodiment, the endogenous gene encodes a tumor antigen. In another embodiment, the endogenous gene is expressed on a tumor cell targeted by the CAR. In yet another embodiment, the endogenous gene encodes CD33 or CD123.

In one embodiment, the modified polypeptide comprises at least one function that is equivalent to the function of the polypeptide encoded by the endogenous gene.

In one embodiment, the cell is obtained from a source selected from the group consisting of peripheral blood mononuclear cells, cord blood cells, bone marrow, lymph node, and spleen.

In one embodiment, the cell is CD34+. In one embodiment, the method of the invention as described herein comprises expanding the cell. In another embodiment, the expanding is conducted prior to the step of introducing the nucleic acid. In another embodiment, the method of the invention as described herein comprises cryopreserving the cell. In yet another embodiment, the method of the invention as described herein further comprises thawing the cryopreserved cell prior to introducing the nucleic acid. In one embodiment, introducing the nucleic acid is conducted by a process selected from the group consisting of transducing the cell, transfecting the cell, and electroporating the cell. In another embodiment, the modified cell differentiates into at least one blood cell type in the subject. In yet another embodiment, the modified cell is capable of self-renewal after administration into the subject.

In one aspect, the invention includes a composition comprising the modified cell generated according to the method described above herein.

In another aspect, the invention includes a pharmaceutical composition comprising the modified cell generated according to the method described above herein and a pharmaceutically acceptable carrier.

In another aspect, the invention includes a method for adoptive cell transfer therapy. The method comprises administering to a subject in need thereof an effective amount of a pharmaceutical composition comprising the modified cell generated according to the method described herein, wherein the subject is administered an effective amount of the cell described herein and a CAR therapy that targets the antigen domain of the polypeptide encoded by the endogenous gene thereby treating the subject.

In yet another aspect, the invention includes a method of treating a condition in a subject in need thereof. The method comprises administering to the subject a therapeutically effective amount of a pharmaceutical composition comprising the modified cell generated according to the method described herein and administering a CAR T cell therapy, wherein the CAR comprises an antigen binding domain that specifically targets the antigen domain of the polypeptide encoded by the endogenous gene, thereby treating the condition.

In one embodiment, the condition is an autoimmune disease. In another embodiment, the autoimmune disease is selected from the group consisting of Acquired Immunodeficiency Syndrome (AIDS), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, pernacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjogren's syndrome, stiff-man syndrome, systemic lupus erythematosus, Takayasu arteritis, temporal arteritis/giant cell arteritis, ulcerative colitis, uveitis, vitiligo, Wegener's granulomatosis, and any combination thereof. In another embodiment, the condition is a cancer. In yet another embodiment, the cancer is selected from the group consisting of breast cancer, prostate cancer, ovarian cancer, cervical cancer, skin cancer, pancreatic cancer, colorectal cancer, renal cancer, liver cancer, brain cancer, lymphoma, leukemia, lung cancer, and any combination thereof.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1A is a graph showing CD33 expression by flow cytometry 5 days after electroporation. FIG. 1B is an image showing mismatch cleavage assay (Surveyor) of PCR of genomic DNA across the gRNA cleavage site. Control cells were electroporated with gRNA against EMX1. Indel %=[1−√{1−(a+b)/(a+b+c)}]*100 (a, b: relative concentration of cut bands, c: relative concentration of full-length band).

FIG. 2A shows a representative plot of CD33 expression by flow cytometry 7 days after electroporation. FIG. 2B is a graph showing indel frequencies measured by TIDE analysis of PCR amplicons spanning the gRNA target site, averaged for different donors; n=4 for RNA and n=2 for RNP.

FIG. 3A shows results from the flow cytometric degranulation assay. FIG. 3B shows results from the luciferase-based killing. In all cases, effectors are CART33 cells. TCM=T cell media alone (negative control); P-I=PMA and ionomycin (positive control); MOLM14 wt=the CD33 expressing AML cell line MOLM14 without genetic modification; D6=MOLM14 KO for CD33; Jurkat=a CD33 negative cell line (an additional negative control).

FIG. 4A is a panel of flow diagrams showing CD33 and CD38 expression in CD33 KO CD34+ cells. FIG. 4B is an image showing mismatch mutation efficiency by surveyor DNA cleavage assay. FIG. 4C is an image showing the Sanger sequencing results of the individual mutations as determined by TOPO cloning. FIG. 4D shows the percentages of CD33 KO cells derived from G-CSF mobilized peripheral blood (mPB), cord blood, and bone marrow.

FIG. 5A is a graph showing a growth curve of control (EMX1) vs. CD33 KO HSCs in vitro culture. FIG. 5B is a graph showing myeloid and erythroid differentiation of control vs. CD33 KO HSCs in methylcellulose medium. FIG. 5C shows cytospun cells from the methylcellulose colonies derived from CD33 KO HSCs showing a typical monocytic and granulocytic morphology compared with control cells.

FIG. 7A shows expression of CD3 and CD45 on CD33 KO HSCs compared to control HSCs, demonstrating that exposure to CART33 is more toxic to control HSC than to CD33KO HSC, and this is quantified in FIG. 7B.

FIG. 9A is a schematic of the CD33 KO process in primary human CD34+ cells derived from G-CSF mobilized peripheral blood. FIG. 9B displays results from a methocult colony formation assay of control or CD33 KO HSPCs. Representative images of colony-forming unit-granulocyte (CFU-G), colony-forming unit-macrophage (CFU-M), and burst-forming unit-erythroid (BFU-E) in both groups are shown. FIG. 9C shows 8-12 week old NSG mice injected with $1-5\times10^5$ control or CD33-KO CD34+ cells and peripheral blood human CD45+ engraftment was measured after 12 weeks (n=68 mice; 6 independent experiments; 6 different donors). FIG. 9D shows gating on the human CD45+ cells from FIG. 9C; B cells (CD19+) and CD3+ T cells (CD3+) were detected with no significant difference between the two groups. FIG. 9E shows human myeloid cells in the CD33 KO HSPC-engrafted mice (gating on hCD45+CD19−CD3− cells) have significantly reduced levels of CD33 expression but no difference in CD11b14+ expression compared to control HSPC-engrafted mice, confirming that loss of CD33 does not impact myeloid differentiation. FIG. 9F illustrates bone marrow harvested after 16 weeks showed equal levels of human CD45+ engraftment in control and CD33 KO HSPC-engrafted mice. FIG. 9G shows levels of human stem cells (hCD45+lin− negative CD34+38−) and myeloid progenitors (hCD45+lin-negative CD34+38+) in the bone marrow of mice engrafted with control or CD33 KO HSPCs. FIG. 9H is a table showing bone marrow was harvested from NSG mice after 16 weeks of primary engraftment and transferred into secondary recipients and analyzed after 12 additional weeks; sustained human engraftment with persistent CD33 KO phenotype is observed. FIG. 9I illustrates bone marrow harvested after 16 weeks of primary engraftment with control and CD33 KO HSPCs, with equal levels of human CD45 expression (top left) and differentiation into lymphoid and myeloid lineages (top right), only differing in the expression of CD33 (bottom left), with no difference in the other myeloid markers CD11b and CD14 (bottom right). FIG. 9J shows expression of CD33 on non-lymphoid human cells (gating for non-T non-B human cells not shown) at the end of the 16 week primary transplant, indicating protracted, stable absence of CD33 in marrows of xenografted mice.

FIG. 10A is a schematic depicting NSG mice engrafted with control or CD33 KO HSPCs were given $5\times10^6$ autologous CART33 cells, and residual human myeloid cells were assessed after 4 weeks (n=30 mice; 2 independent experiments; 2 different donors). FIG. 10B shows CD33 is eliminated in the peripheral blood of mice treated with CART33, which leads to ablation of myeloid cells (CD11b+CD14+) in the control HSPC-engrafted mice, while in the CD33 KO HSPC-engrafted mice the myeloid cells are sustained. FIG. 10C illustrates myeloid cells are detected in the peripheral blood, spleen, and bone marrow of the CD33 KO HSPC-engrafted mice after CART33 treatment, in contrast to the myeloablation seen in control HSPC-engrafted mice. FIG. 10D shows human progenitor cells are significantly increased in CD33 KO HSPC-engrafted mice after CART33 treatment compared to controls.

FIGS. 11A-11E are a series of plots and images showing CART33 can eradicate AML while sparing CD33 KO HSPCs. FIG. 11A is a schematic illustrating that NSG mice were first engrafted with control or CD33 KO HSPCs, then injected with Molm14, an AML cell line engineered to express green fluorescent protein and luciferase, followed by CART33 treatment (n=8 mice). AML disease burden was measured by bioluminescent imaging (BLI), while human HSPCs were measured by flow cytometry of the peripheral blood. FIG. 11B is a series of BLI images showing that both control and CD33 KO HSPC-engrafted mice achieve AML disease remission after CART33 treatment. FIG. 11C shows tumor burden over time as measured by BLI; each line represents one mouse. Dotted line represents background levels of radiance. FIG. 11D shows CD33 KO HSPC-engrafted mice show persistent CD14+ myeloid cells after CART33 treatment of AML in the peripheral blood (PB), spleen, and bone marrow (BM), in contrast to controls. FIG. 11E shows human progenitor cells are spared from CART33-mediated toxicity in the CD33 KO HSPC group only.

FIGS. 12A-12F are a series of plots and images showing CD33 KO HSPC progeny have no functional defects. FIG. 12A illustrates cytospin and Diff-Quick staining of human cells obtained from HSPC-engrafted mouse bone marrow show characteristic morphologic features of normal stem cell (blast), myeloid progenitor (promyelocyte), and terminal effector cells (monocytes and neutrophils). FIG. 12B shows control or CD33 KO HSPCs differentiated in vitro with myeloid cytokines (SCF, TPO, Flt3L, IL-6, GM-CSF, IL-3) and incubated with pHrodo green *E. coli* bioparticles that have green fluorescence when acidified in the phagosome; percent phagocytosis was measured by flow cytometry. Top, representative flow plots from control and CD33 KO cells; bottom, quantification of phagocytosis from 2 independent experiments with 4 different donors. FIGS. 12C-12D show control and CD33 KO CD34+ cells from 5 different mobilized peripheral blood donors were differentiated in vitro and gene expression was analyzed by RNA-seq. FIG. 12C depicts fold-changes of differentially expressed genes shown as a heat map, with each row corresponding to genes and each column representing one sample from control (ctrl) or CD33 KO (KO); numbers indicate donor of origin. Columns and rows are organized by hierarchical clustering; dendrogram branch length represents distances between samples and clusters. FIG. 12D is a log-scale scatter plot of mean gene expression values of control and CD33 KO samples. The coefficient of determination (R2) value is shown. FIG. 12E shows mice engrafted with control or CD33 KO HSPCs were injected with rhG-CSF and absolute numbers of peripheral blood human monocytes (CD11b+14+) and neutrophils (CD11b+14−) were measured; fold-change of cell numbers compared to baseline levels are shown. FIG. 12F illustrates mice engrafted with control or CD33 KO HSPCs were injected with lipopolysaccharide and serum levels of human cytokines were measured.

FIG. 13A is a table showing the top 12 off-target sites predicted in silico from two web-based tools. FIG. 13B, top panel, shows that SIGLEC22P, a pseudogene, has a high degree of homology to the CD33 gene, with a 100% identical binding site of the CD33-targeted gRNA used herein. FIG. 13B, bottom panel, shows no mutations detected by Surveyor mismatch assay in other SIGLEC genes, while a high degree of on-target mutations are found in CD33 and SIGLEC22P.

FIG. 14A shows the experimental schema, whereby rhesus CD34+ HSPC are mobilized using G-CSF and plerixafor, removed by apheresis, and gene edited with CRISPR/Cas9-based gene knockout of CD33. In the meantime, the monkey is conditioned with irradiation (TBI) and following that, receives a re-infusion of the edited HSPC. On the top right panel, flow cytometric evaluation of CD33 expression in in vitro differentiated HSPC is shown in control and KO cells, and TIDE analysis of sequencing of the CD33 locus is shown on the bottom right panel. FIG. 14B shows expression of CD33 on selected sub-populations from the PB of the animal transplanted in FIG. 14A.

DETAILED DESCRIPTION

Definitions

Figure 1A:
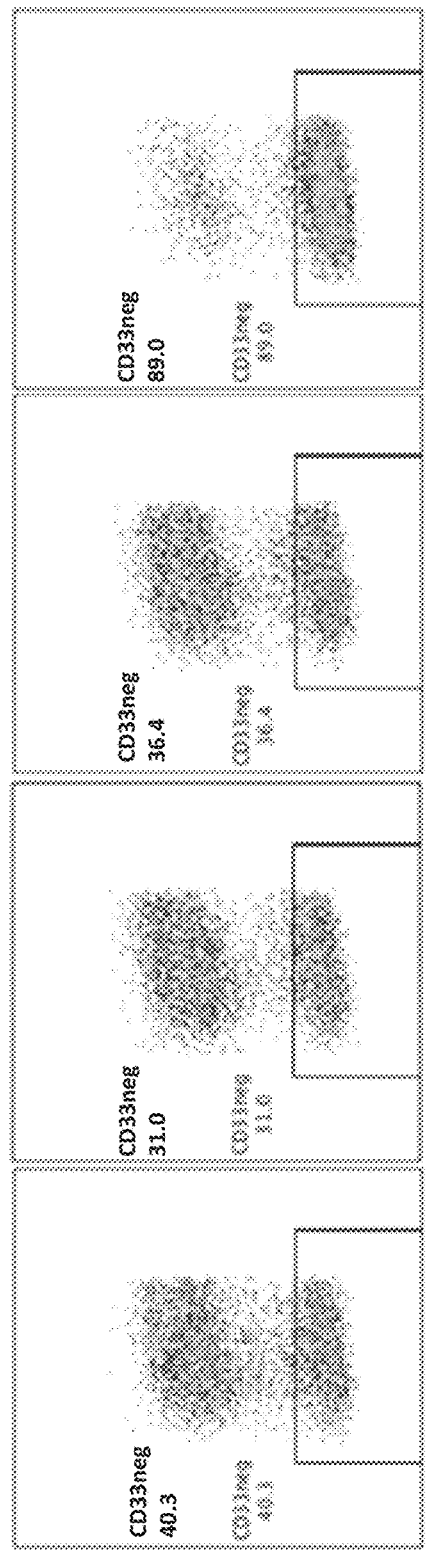
FIGS. 1A-1B are a set of plots and images showing the CD33 gRNA screen. Molm14 cells were electroporated with Cas9 mRNA on day 1 and gRNAv1-5 on day 2.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies (scFv) and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "auto-antigen" means, in accordance with the present invention, any self-antigen which is recognized by the immune system as being foreign. Auto-antigens comprise, but are not limited to, cellular proteins, phosphoproteins, cellular surface proteins, cellular lipids, nucleic acids, glycoproteins, including cell surface receptors.

The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia areata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. In certain embodiments, the cancer is medullary thyroid carcinoma.

The term "chimeric antigen receptor" or "CAR," as used herein, refers to an artificial T cell receptor that is engineered to be expressed on an immune effector cell and specifically bind an antigen. CARs may be used as a therapy with adoptive cell transfer. T cells are removed from a patient and modified so that they express the receptors specific to a particular form of antigen. In some embodiments, the CARs have been expressed with specificity to a tumor associated antigen, for example. CARs may also comprise an intracellular activation domain, a transmembrane domain and an extracellular domain comprising a tumor associated antigen binding region. In some aspects, CARs comprise single-chain variable fragments (scFv) derived from monoclonal antibodies. The specificity of CAR designs may be derived from ligands of receptors (e.g., peptides). In some embodiments, a CAR can target cancers by redirecting the specificity of a T cell expressing the CAR specific for tumor associated antigens.

The term "cleavage" refers to the breakage of covalent bonds, such as in the backbone of a nucleic acid molecule. Cleavage can be initiated by a variety of methods, including, but not limited to, enzymatic or chemical hydrolysis of a phosphodiester bond, Both single-stranded cleavage and double-stranded cleavage are possible. Double-stranded cleavage can occur as a result of two distinct single-stranded cleavage events. DNA cleavage can result in the production of either blunt ends or staggered ends. In certain embodiments, fusion polypeptides may be used for targeting cleaved double-stranded DNA.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody can be replaced with other amino acid residues from the same side chain family and the altered antibody can be tested for the ability to bind antigens using the functional assays described herein.

The term "CRISPR/CAS," "clustered regularly interspaced short palindromic repeats system," or "CRISPR" refers to DNA loci containing short repetitions of base sequences. Each repetition is followed by short segments of spacer DNA from previous exposures to a virus. Bacteria and archaea have evolved adaptive immune defenses termed. CRISPR-CRISPR-associated (Cas) systems that use short RNA to direct degradation of foreign nucleic acids. In bacteria, the CRISPR system provides acquired immunity against invading foreign DNA via RNA-guided DNA cleavage.

In the type II CRISPR/Cas system, short segments of foreign DNA, termed "spacers" are integrated within the CRISPR genomic loci and transcribed and processed into short CRISPR RNA (crRNA). These crRNAs anneal to trans-activating crRNAs (tracrRNAs) and direct sequence-specific cleavage and silencing of pathogenic DNA by Cas proteins. Recent work has shown that target recognition by the Cash) protein requires a "seed" sequence within the crRNA and a conserved dinucleotide-containing protospacer adjacent motif (PAM) sequence upstream of the crRNA-binding region.

To direct Cas9 to cleave sequences of interest, crRNA-tracrRNA fusion transcripts, hereafter referred to as "guide RNAs" or "gRNAs" may be designed, from human U6 polymerase III promoter, CRISPR/CAS mediated genome editing and regulation, highlighted its transformative potential for basic science, cellular engineering and therapeutics.

The term "CRISPRi" refers to a CRISPR system for sequence specific gene repression or inhibition of gene expression, such as at the transcriptional level.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "downregulation" as used herein refers to the decrease or elimination of gene expression of one or more genes or a portion thereof.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expand" as used herein refers to increasing in number, as in an increase in the number of cells. In one embodiment, the cells that are expanded ex vivo increase in number relative to the number originally present in the culture. In another embodiment, the cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

The term "hematopoietic stem cell" or "HSC" refers to an undifferentiated hematopoietic cell that is capable of differentiating into all blood cell types, myeloid and lymphoid cells. The HSC may reside in the bone marrow or be found elsewhere e.g. peripheral blood.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

The term "immune response" as used herein is defined as a cellular response to an antigen that occurs when lymphocytes identify antigenic molecules as foreign and induce the formation of antibodies and/or activate lymphocytes to remove the antigen.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "knockout" or "KO" as used herein refers to the ablation of gene expression of one or more genes.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" tumor antigen or "overexpression" of a tumor antigen is intended to indicate an abnormal level of expression of a tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

The term "portion thereof" refers to a part of or a fragment of the whole.

The term "hematopoietic progenitor cell" refers to an undifferentiated hematopoietic cell capable of differentiating into at least one blood cell type to several blood cell types, but not all blood cells like a HSC. Examples of hematopoietic progenitor cells include, but are not limited to, a common myeloid progenitor cell, megakaryocyte-erythrocyte progenitor cell, granulocyte-macrophage progenitor cell, monocyte-dendritic progenitor cell, and a common lymphoid progenitor cell.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

A "Sendai virus" refers to a genus of the Paramyxoviridae family. Sendai viruses are negative, single stranded RNA viruses that do not integrate into the host genome or alter the genetic information of the host cell. Sendai viruses have an exceptionally broad host range and are not pathogenic to humans. Used as a recombinant viral vector, Sendai viruses are capable of transient but strong gene expression.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the plasma membrane of a cell.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-beta, and/or reorganization of cytoskeletal structures, and the like.

"Substantially complementary," as used herein, refers to sequences of nucleotides where a majority or all of the bases in the primer sequence are complementary, or one or more bases are non-complementary, or mismatched.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

A "target site" or "target sequence" refers to a genomic nucleic acid sequence that defines a portion of a nucleic acid to which a binding molecule may specifically bind under conditions sufficient for binding to occur.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The invention described herein includes compositions and methods of generating modified hematopoietic stem or progenitor cells that have decreased expression of an endogenous gene or a portion thereof. The endogenous gene encodes a polypeptide comprising an antigen domain targeted by a CAR or by any other antibody-based modality such as a monoclonal antibody, scFv, or bi-specific antibody (e.g. BITE). The endogenous gene or a portion thereof is downregulated via gene editing such that the modified hematopoietic stem or progenitor cells are rendered resistant to CART cell or other antigen-specific therapy.

Methods

One aspect of the invention includes a method of protecting a hematopoietic stem or progenitor cell from a chimeric antigen receptor (CAR) T cell therapy or other antigen-specific therapy in a subject in need thereof. The method comprises administering a modified hematopoietic stem or progenitor cell. The stem or progenitor cell comprises a nucleic acid capable of decreasing expression of an endogenous gene or a portion thereof and the endogenous gene encodes a polypeptide comprising an antigen domain targeted by a CAR. In one embodiment, the invention may further comprise administering the CART therapy to the subject in need thereof.

The modified cell may further comprise a modified endogenous gene that encodes a modified polypeptide lacking the antigen domain targeted by the CAR. The modified polypeptide may comprise at least one function that is equivalent to the function of the polypeptide encoded by the endogenous gene.

The invention also includes a method for generating a modified hematopoietic stem or progenitor cell. The method comprises introducing a nucleic acid capable of decreasing expression of an endogenous gene or a portion thereof into the cell, wherein the endogenous gene encodes a polypeptide comprising an antigen domain targeted by a chimeric antigen receptor (CAR). The invention may further comprise obtaining a cell from a subject in need of CAR T cell therapy. The cell may be obtained from peripheral blood mononuclear cells, cord blood cells, bone marrow, lymph nodes, and/or a spleen. The cell may be CD34+.

In certain embodiments of the invention, the nucleic acid capable of decreasing endogenous gene expression is a CRISPR system. The CRISPR system may comprise a Cas expression vector and a guide nucleic acid sequence specific for the endogenous gene and/or a Cas9 protein complexed with a guide nucleic acid sequence specific for the endogenous gene. The CRISPR system may comprise an inducible promoter. The hematopoietic stem or progenitor cell may be exposed to an agent that activates the inducible promoter in the Cas expression vector.

In certain embodiments, the endogenous gene may encode a tumor antigen and/or may be expressed on a tumor cell targeted by the CAR and/or may encode CD33, CD123, CD19, or CD22. A modified endogenous gene may be introduced into the modified cell, wherein the modified endogenous gene encodes a modified polypeptide lacking the antigen domain targeted by the CAR. The modified polypeptide may comprise at least one function that is equivalent to the function of the polypeptide encoded by the endogenous gene.

Certain embodiments of the invention further comprise expanding the cells. Expansion may be prior to the step of introducing the nucleic acid. The cells may be cryopreserved then thawed prior to introducing the nucleic acids. The nucleic acid may be introduced by transducing the cell, or transfecting the cell, or electroporating the cell.

The invention also includes a modified cell that is generated according to the methods described herein. A pharmaceutical composition comprising the modified cell and a pharmaceutically acceptable carrier generated according to the methods described herein are also included in the invention.

CRISPR/Cas

Genome editing using programmable nucleases enables precise editing at specific genomic loci, which can be used to remove deleterious mutations or insert protective mutations. To date, there are three major classes of nucleases—zinc finger nucleases (ZFNs), transcription activator-like effector nucleases (TALENs), and clustered, regularly interspaced, short palindromic repeat (CRISPR)-associated nucleases. Of these, CRISPR-associated nucleases have proven to be markedly superior to the others in terms of the ease and simplicity of use.

The CRISPR/Cas system is a facile and efficient system for inducing targeted genetic alterations. Target recognition by the Cas9 protein requires a 'seed' sequence within the guide RNA (gRNA) and a conserved di-nucleotide containing protospacer adjacent motif (PAM) sequence upstream of the gRNA-binding region. The Cas9 protein, under direction from the gRNA, binds to its target DNA sequence and cuts both strands of the DNA at a specific locus. This double-stranded DNA break is repaired by either non-homologous end joining (NHEJ) or homology-directed repair (HDR). NHEJ frequently causes small insertions or deletions (indels) at the breakage site that can lead to a frameshift mutation of the protein encoded by the gene. HDR utilizes a repair template that is copied into the gene, thus engineering specific mutations.

The CRISPR/CAS system can thereby be engineered to cleave virtually any DNA sequence by redesigning the gRNA in cell lines (such as 293T cells), primary cells, CAR T cells, and stem and progenitor cells. In one aspect, the invention includes a modified hematopoietic stem or progenitor cell comprising a nucleic acid capable of decreasing expression of an endogenous gene or a portion thereof, wherein the endogenous gene encodes a polypeptide comprising an antigen domain targeted by a chimeric antigen receptor (CAR).

One example of a CRISPR/Cas system used to inhibit gene expression, CRISPRi, is described in U.S. Publication No.: 2014/0068797. CRISPRi induces permanent gene disruption that utilizes the RNA-guided Cas9 endonuclease to introduce DNA double stranded breaks which trigger error-prone repair pathways to result in frame shift mutations. A catalytically dead Cas9 lacks endonuclease activity. When coexpressed with a guide RNA, a DNA recognition complex is generated that specifically interferes with transcriptional elongation, RNA polymerase binding, or transcription factor binding. This CRISPRi system efficiently represses expression of targeted genes.

CRISPR/Cas gene disruption occurs when a guide nucleic acid sequence specific for a target gene and a Cas endonuclease are introduced into a cell and form a complex that enables the Cas endonuclease to introduce a double strand break at the target gene. The CRISPR/CAS system can also simultaneously target multiple genomic loci by co-expressing a single CAS9 protein with two or more gRNAs, making this system uniquely suited for multiple gene editing or synergistic activation of target genes. In one aspect, a modified hematopoietic stem or progenitor cell is generated by introducing a nucleic acid capable of decreasing expression of an endogenous gene or a portion thereof into the cell, wherein the endogenous gene encodes a polypeptide comprising an antigen domain targeted by a chimeric antigen receptor (CAR). In such an embodiment, the nucleic acid capable of decreasing expression of the endogenous gene or a portion thereof is a CRISPR system. In some embodiments, the CRISPR system includes a Cas expression vector and a guide nucleic acid sequence specific for the endogenous gene. In another embodiment, the Cas expression vector induces expression of Cas9 endonuclease. Other endonucleases may also be used, including but not limited to, T7, Cas3, Cas8a, Cas8b, Cas10d, Cse1, Csy1, Csn2, Cas4, Cas10, Csm2, Cmr5, Fok1, other nucleases known in the art, and any combination thereof.

In one embodiment, introducing the CRISPR system comprises introducing an inducible CRISPR system. The CRISPR system may be induced by exposing the hematopoietic stem or progenitor cell to an agent that activates an inducible promoter in the CRISPR system, such as the Cas expression vector. In such an embodiment, the Cas expression vector includes an inducible promoter, such as one that is inducible by exposure to an antibiotic (e.g., by tetracycline or a derivative of tetracycline, for example doxycycline). However, it should be appreciated that other inducible promoters can be used. The inducing agent can be a selective condition (e.g., exposure to an agent, for example an antibiotic) that results in induction of the inducible promoter. This results in expression of the Cas expression vector.

The guide nucleic acid sequence is specific for a gene and targets that gene for Cas endonuclease-induced double strand breaks. The sequence of the guide nucleic acid sequence may be within a locus of the gene. In one embodiment, the guide nucleic acid sequence is at least 10, 11, 12, 13, 14, 15, 16, 17, 18, 19, 20, 21, 22, 23, 24, 25, 26, 27, 30, 31, 32, 33, 34, 35, 36, 37, 38, 39, 40 or more nucleotides in length.

The guide nucleic acid sequence may be specific for any gene, such as an endogenous gene that would reduce immunogenicity or reduce sensitivity to a CART therapy. The endogenous gene of the present invention encodes a polypeptide comprising an antigen domain targeted by a CAR. In one embodiment, the guide nucleic acid sequence is specific for the endogenous gene that encodes a tumor antigen. In yet another embodiment, the guide nucleic acid sequence is specific for the endogenous gene that encodes CD33 or CD123.

The guide nucleic acid sequence includes a RNA sequence, a DNA sequence, a combination thereof (a RNA-DNA combination sequence), or a sequence with synthetic nucleotides. The guide nucleic acid sequence can be a single molecule or a double molecule. In one embodiment, the guide nucleic acid sequence comprises a single guide RNA.

Endogenous Gene Targets

CARs are typically used as a therapy in adoptive cell transfer. The CAR is an artificial receptor expressed on a T cell that is engineered to specifically bind to an antigen and activate the T cell as an immune effector cell. In many instances, the antigen targeted by the CART cells is an endogenous gene that is expressed on normal and diseased cells. Thus, the CART cells target both normal and diseased cells for elimination.

The target of the CAR of the present invention encodes an endogenous (to the cell) polypeptide comprising an antigen domain expressed on cells. A CAR usually includes an extracellular domain that comprises an antigen binding domain. In some embodiments, the antigen binding domain of the CAR specifically binds to the antigen on a target cell. In other embodiments, the antigen binding domain of the CAR specifically binds to a tumor antigen. In one embodiment, the endogenous gene is expressed on a tumor cell targeted by the CAR. In some embodiments, the endogenous gene encodes a cell surface molecule comprising an antigen domain targeted by the CAR. Cell surface molecules include endogenous molecules that may act as a binding partner associated with viral, bacterial and parasitic infections.

Examples of endogenous genes may include, but are not limited to a gene that encodes CD19; CD123; CD22; CD30; CD171; CS-1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRvIII); ganglioside G2 (GD2); ganglioside GD3 (aNeu5Ac(2-8)aNeu5Ac(2-3)bD-Galp(1-4)bDGlcp(1-1)Cer); TNF receptor family member B cell maturation (BCMA); Tn antigen ((Tn Ag) or (GalNAcα-Ser/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac(2-3)bDGalp(1-4) bDGlcp(1-1)Cer); transglutaminase 5 (TGS5); high molecular weight-melanoma-associated antigen (HMW-MAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRCSD); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1 (PCTA-1 or Galectin 8), melanoma antigen recognized by T cells 1 (MelanA or MART1); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP1B1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAXS); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

The choice of endogenous gene depends on the expression of the endogenous gene in normal cells, the presence of the expressed endogenous gene product on the surface of normal cells, and the effect CART therapy has on normal cells. For example, the endogenous gene may be highly expressed on diseased cells and have limited expression in normal cells.

In another example, the endogenous gene may be widely expressed in normal blood cells and the CART therapy would potentially target all those cells in addition to diseased cells. In such circumstances, introduction of a modified endogenous gene may be useful. Introduction of a modified endogenous gene may be particularly useful when expression of the endogenous gene is critical for the health of a non-diseased cell, such as a hematopoietic stem or progenitor cell. In one embodiment, the method of generating the modified cell described herein comprises decreasing expression of a portion of the endogenous gene, such as the portion comprising the antigen domain targeted by the CAR. In such an embodiment, the method can comprise introducing a modified endogenous gene that encodes a modified polypeptide lacking the antigen domain targeted by the CAR. In another embodiment, the modified cell described herein comprises a modified endogenous gene that encodes a modified polypeptide lacking the antigen domain targeted by the CAR. In yet another embodiment, the modified polypeptide comprises at least one function that is equivalent to the function of the polypeptide encoded by the endogenous gene. Thus, the modified cell expresses the modified endogenous gene, while maintaining resistance to CART cell therapy.

Introduction of Nucleic Acids

Methods of introducing a nucleic acid into the hematopoietic stem or progenitor cell include physical, biological and chemical methods. Physical methods for introducing a polynucleotide, such as RNA, into a host cell include calcium phosphate precipitation, lipofection, particle bombardment, microinjection, electroporation, and the like. RNA can be introduced into target cells using commercially available methods which include electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany). RNA can also be introduced into cells using cationic liposome mediated transfection using lipofection, using polymer encapsulation, using peptide mediated transfection, or using biolistic particle delivery systems such as "gene guns" (see, for example, Nishikawa, et al. Hum Gene Ther., 12(8):861-70 (2001).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce the nucleic acid into the cell, a variety of assays may be performed to confirm the presence of the nucleic acid in the cell. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

In one aspect, the invention includes a method for generating a modified hematopoietic stem or progenitor cell comprising introducing a nucleic acid capable of decreasing endogenous gene expression into the cell, wherein the endogenous gene encodes a polypeptide comprising an antigen domain to be targeted by a chimeric antigen receptor (CAR). In one embodiment, the method further comprises introducing a modified endogenous gene into the modified cell, wherein the modified endogenous gene encodes a modified polypeptide lacking the antigen domain targeted by the CAR. In such an embodiment, one nucleic acid may be introduced using the same or a different method from that used to introduce the modified endogenous gene into the cell.

RNA

In one embodiment, the nucleic acid introduced into the cell comprises a RNA. In another embodiment, at least one component of the CRISPR system comprises RNA. In yet another embodiment, the guide nucleic acid sequence is a RNA. In another embodiment, the RNA comprises in vitro transcribed RNA or synthetic RNA. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA.

PCR can be used to generate a template for in vitro transcription of RNA which is then introduced into cells. Methods for performing PCR are well known in the art. Primers for use in PCR are designed to have regions that are substantially complementary to regions of the DNA to be used as a template for the PCR. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Chemical structures that have the ability to promote stability and/or translation efficiency of the RNA may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the template. Alternatively, UTR sequences that are not endogenous for the template can be added by incorporating the UTR sequences into the forward and reverse primers or by any other modifications of the template. The use of UTR sequences that are not endogenous to the template can be useful for modifying the stability and/or translation efficiency of the RNA. For example, it is known that AU-rich elements in 3' UTR sequences can decrease the stability of RNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many RNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the RNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

The RNAs described herein may be introduced into the cell by a variety of methods known in the art. In some embodiments, the RNA is electroporated into the cells. In one embodiment, the CRISPR system comprises a RNA that is electroporated into the cells. In yet another embodiment, the CRISPR system comprises at least one guide nucleic acid sequence that is a RNA and electroporated into the cells.

The disclosed methods can be applied to the modulation of cell activity in order to provide therapy to the subject in the fields of cancer, acute and chronic infections, and autoimmune diseases. The disclosed methods can involve targeting stem cells, and also can include methods for assessing the ability of the genetically modified cell to kill a target cancer cell.

The methods also provide the ability to control the level of expression over a wide range by changing, for example, the promoter or the amount of input RNA, making it possible to individually regulate the expression level.

One advantage of RNA transfection methods of the invention is that RNA transfection is essentially transient and a vector-free. A RNA transgene can be delivered to a cell and expressed therein, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of the cells with in vitro-transcribed RNA (IVT-RNA) makes use of two different strategies both of which have been successively tested in various animal models. Cells are transfected with in vitro-transcribed RNA by means of lipofection or electroporation. It is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

In another aspect, the RNA construct is delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

Sources of HSCs or Progenitor Cells

Prior to expansion, a source of the cells is obtained from a subject. Non-limiting examples of subjects include humans, dogs, cats, mice, rats, non-human primates, swine and transgenic species thereof. Preferably, the subject is a human. The cells can be obtained from a number of sources, including peripheral blood mononuclear cells, bone marrow, cord blood, lymph node tissue, spleen tissue, umbilical cord, and tumors. In certain embodiments, a HSC or progenitor cell line available in the art, may be used. In certain embodiments, the cells can be obtained from a unit of blood collected from a subject using any number of techniques known to the skilled artisan, such as Ficoll separation. In one embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, the cells are isolated from peripheral blood by lysing the red blood cells and depleting the monocytes, for example, by centrifugation through a PERCOLL™ gradient. Alternatively, the cells can be isolated from umbilical cord. In any event, a specific subpopulation of HSC or progenitor cells can be further isolated by positive or negative selection techniques.

The cord blood mononuclear cells so isolated can be depleted of cells expressing certain antigens, including, but not limited to, CD4, CD5, CD8, CD11b, CD14, CD19, CD24, CD45, CD56, and CD66b. Depletion of these cells can be accomplished using an isolated antibody, a biological sample comprising an antibody, such as ascites, an antibody bound to a physical support, and a cell bound antibody.

Enrichment of a cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD34+ cells by negative selection, a monoclonal antibody cocktail typically includes antibodies to CD4, CD5, CD8, CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

The cells can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In one embodiment, the cell is obtained from cells selected from the group consisting of peripheral blood mononuclear cells, cord blood cells, bone marrow, lymph nodes, and a spleen. In another embodiment, the cell is CD34+.

Expansion of HSC or Progenitor Cells

The present invention includes a population of cells comprising the modified cell described herein. In one embodiment, the method for generating the modified cell described herein also includes expanding the cell or the modified cell. In one embodiment, the expansion is prior to the step of introducing the nucleic acid. In yet another embodiment, the expansion is prior to the step of introducing the nucleic acid. In some embodiments, the cells disclosed herein can be expanded by about 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater, and any and all whole or partial integers therebetween. In one embodiment, the cells are expanded in the range of about 20 fold to about 50 fold.

The cells can be incubated in cell medium in a culture apparatus for a period of time or until the cells reach high cell density for optimal passage before passing the cells to another culture apparatus. The culturing apparatus can be of any culture apparatus commonly used for culturing cells in vitro. The cell medium may be replaced during the culture of the cells at any time. Preferably, the cell medium is replaced about every 2 to 3 days. The cells are then harvested from the culture apparatus whereupon the cells can be used immediately or cryopreserved to be stored for use at a later time. In one embodiment, the invention includes cryopreserving the expanded cells. The cryopreserved cells are thawed prior to introducing nucleic acids into the cell.

In another embodiment, the method further comprises isolating the cell and expanding the cell. In another embodiment, the invention further comprises cryopreserving the cell prior to expansion. In yet another embodiment, the invention further comprises thawing the cryopreserved cell prior to introducing the nucleic acids.

The culturing step as described herein (contact with agents as described herein) can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The culturing step as described further herein (contact with agents as described herein) can be longer, for example 1, 2, 3, 4, 5, 6, 7, 8, 9, 10, 11, 12, 13, 14, or more days.

Various terms are used to describe cells in culture. Cell culture refers generally to cells taken from a living organism and grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but is not limited to the seeding density, substrate, medium, and time between passaging.

In one embodiment, the cells may be cultured for several hours (about 3 hours) to about 14 days or any hourly integer value in between. Conditions appropriate for HSC or progenitor cell culture include an appropriate media (e.g., Minimal Essential Media or RPMI Media 1640 or, X-vivo 15, (Lonza)) that may contain factors necessary for proliferation and viability, such as but not limited to, serum (e.g., fetal bovine or human serum), GM-CSFinsulin, IFN-gamma, interleukin-1 (IL-1), IL-3, IL-4, IL-6, IL-7, IL-10, IL-12, IL-15, SCF, TGF-beta, TNF-α and TPO. or any other additives for the growth of cells known to the skilled artisan. In one embodiment, the cell culture includes IL-3, IL-6, GM-CSF, SCF and TPO. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of HSC or progenitor cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

The medium used to culture the cells may include an agent that can stimulate the modified cells to expand. The cell modified by the methods disclosed herein can be expanded approximately 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater. In one embodiment, the modified cell expands in the range of about 20 fold to about 50 fold, or more by culturing the modified cell.

Therapy

The modified cells described herein may be included in a composition for therapy. The composition may include a pharmaceutical composition and further include a pharmaceutically acceptable carrier. A therapeutically effective amount of the pharmaceutical composition comprising the modified cells may be administered.

In one aspect, the invention includes a method of protecting a hematopoietic stem or progenitor cell from a chimeric antigen T cell (CART) therapy in a subject in need thereof, the method comprising administering a modified hematopoietic stem or progenitor cell, wherein the stem or progenitor cell comprises a nucleic acid capable of decreasing expression of an endogenous gene and the endogenous gene encodes a polypeptide comprising an antigen domain targeted by a chimeric antigen receptor (CAR).

In another aspect, the invention includes a method for adoptive cell transfer therapy, the method comprising administering to a subject in need thereof an effective amount of a pharmaceutical composition comprising the modified cell generated according to a method described herein, wherein the subject is administered an effective amount of the cell described herein and a CAR therapy that targets the antigen domain of the polypeptide encoded by the endogenous gene thereby treating the subject.

In another aspect, the invention includes a method of treating a condition in a subject in need thereof, the method comprising administering to the subject a therapeutically effective amount of a pharmaceutical composition comprising the modified cell generated according to a method described herein and administering a CAR therapy, wherein the CAR comprises an antigen binding domain that specifically targets the antigen domain of the polypeptide encoded by the endogenous gene, thereby treating the condition.

The modified cells described herein can be administered to a subject, preferably a mammal, even more preferably a human. In one embodiment, the modified cell differentiates into at least one blood cell type in the subject. In another embodiment, the modified cell is capable of self-renewal after administration into the subject.

In one embodiment, the condition is a cancer. Examples of various cancers include but are not limited to breast cancer, prostate cancer, ovarian cancer, cervical cancer, skin cancer, pancreatic cancer, colorectal cancer, renal cancer, liver cancer, brain cancer, lymphoma, leukemia, lung cancer and the like. In certain embodiments, the cancer is a leukemia, such as acute myeloid leukemia.

Further, the modified cells can be administered to a subject, preferably a mammal, even more preferably a human, to suppress an immune reaction. The modified cells can be administered to suppress an immune reaction, such as those common to autoimmune diseases such as diabetes, psoriasis, rheumatoid arthritis, multiple sclerosis, GVHD, enhancing allograft tolerance induction, transplant rejection, and the like. In addition, the cells of the present invention can be used for the treatment of any condition in which a diminished or otherwise inhibited immune response, especially a cell-mediated immune response, is desirable to treat or alleviate the disease.

Further, the modified cells can be administered to a subject, preferably a mammal, even more preferably a human, to treat a condition, such as an autoimmune disease. Examples of various autoimmune diseases include but are not limited to Examples of autoimmune disease include but are not limited to, Acquired Immunodeficiency Syndrome (AIDS, which is a viral disease with an autoimmune component), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, pernacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjogren's syndrome, stiff-man syndrome, systemic lupus erythematosus, Takayasu arteritis, temporal arteritis/giant cell arteritis, ulcerative colitis, uveitis, vitiligo and Wegener's granulomatosis.

The cells generated as described herein can also be modified and used to treat inflammatory disorders. Examples of inflammatory disorders include but are not limited to, chronic and acute inflammatory disorders. Examples of inflammatory disorders include Alzheimer's disease, asthma, atopic allergy, allergy, atherosclerosis, bronchial asthma, eczema, glomerulonephritis, graft vs. host disease, hemolytic anemias, osteoarthritis, sepsis, stroke, transplantation of tissue and organs, vasculitis, diabetic retinopathy and ventilator induced lung injury.

In another embodiment, the modified cell described herein may be used for the manufacture of a medicament for the treatment of an immune response in a subject in need thereof.

Cells of the invention can be administered in dosages and routes and at times to be determined in appropriate preclinical and clinical experimentation and trials. Cell compositions may be administered multiple times at dosages within these ranges. Administration of the cells of the invention may be combined with other methods useful to treat the desired disease or condition as determined by those of skill in the art.

The cells of the invention to be administered may be autologous, allogeneic or xenogeneic with respect to the subject undergoing therapy.

The administration of the cells of the invention may be carried out in any convenient manner known to those of skill in the art. The cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i. v.) injection, or intraperitoneally. In other instances, the cells of the invention are injected directly into a site of inflammation in the subject, a local disease site in the subject, a lymph node, an organ, a tumor, and the like.

Pharmaceutical Compositions

Pharmaceutical compositions of the present invention may comprise the modified cell as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-immune response effective amount", "an immune response-inhibiting effective amount", or "therapeutic amount" is indicated, the precise amount of the compositions of the present invention to be administered can be determined by a physician with consideration of individual differences in age, weight, immune response, and condition of the patient (subject). It can generally be stated that a pharmaceutical composition comprising the modified cells described herein may be administered at a dosage of $10^4$ to $10^9$ cells/kg body weight, preferably $10^5$ to $10^6$ cells/kg body weight, including all integer values within those ranges. Cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments of the present invention, the cells are expanded and modified using the methods described herein, or other methods known in the art where the cells are expanded to therapeutic levels, and administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the modified cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAM-PATH. In another embodiment, the cell compositions of the present invention are administered following B-cell ablative therapy such as agents that react with CD20, e.g., Rittman. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAM-PATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The materials and methods employed in these experiments are now described.

Construct Cloning.

Human codon optimized Cas9 expressed under the T7 promoter was kindly provided by Dr. Yangbing Zhao. Cas9 mRNA was in vitro transcribed using the mMessage mMachine T7 Ultra kit (Ambion, AM1345). The guide RNAs (gRNAs) were cloned into pUC57-sgRNA plasmid (Addgene 51132) using standard molecular biology techniques. gRNAs were in vitro transcribed using the T7-Scribe Standard RNA IVT kit (Cellscript, C-AS2607). RNA was purified using the RNeasy Mini Kit (Qiagen, 74104).

Primary CD34+ Cell Isolation.

Frozen CD34+ cells were purchased from the Stem Cell and Xenograft Core at the University of Pennsylvania. Alternatively, G-CSF mobilized peripheral blood from autologous stem cell donors were obtained from clinical specimens that were no longer in use at the Hospital of the University of Pennsylvania, and CD34+ selection was performed using the CD34 Microbead Kit (Miltenyi, 130-046-702). CD34+ cell purity was confirmed by flow cytometry to be >95%. Cells were rested overnight prior to electroporation.

Cell Culture.

Molm14 cells were cultured in RPMI-1640 medium supplemented with 10% FBS (R10). CD34+ cells were cultured in StemSpan SFEM (Stem Cell Technologies, 09650) supplemented with human cytokines (SCF 100 ng/ul, Flt3 ligand 100 ng/ul, TPO 50 ng/ul, IL-6 50 ng/ul).

Electroporation.

Molm14 or CD34+ cells were washed once and resuspended in Opti-MEM and electroporated with Cas9 mRNA with the BTX ECM 830 Square Wave Electroporation System (Harvard Apparatus) using a single pulse of 400V and 5 msec. Cells were incubated at 32° C. overnight and re-electroporated with gRNA the next day using the same machine and settings. Cells were kept at 32'C until the following day, after which they were cultured at 37'C until analysis. Alternatively, CD34+ cells were electroporated once with Cas9 protein (PNA Bio, CP02) complexed with a CD33-targeted gRNA using the same settings. Cells were incubated at 32'C overnight and then injected into NSG mice or kept at 37'C for further analysis.

Mice Transplantation Studies.

For in vivo studies, 8-12 week old NOD-SCID-IL2rg$^{-/-}$ (NSG) mice were originally obtained from Jackson Laboratories and purchased from the Stem Cell and Xenograft Core at the University of Pennsylvania. Mice were injected with busulfan 30 mg/kg and the following day 1-5×10$^5$ control or CD33 KO HSPCs were injected. Mice were bled retro-orbitally every 4 weeks to monitor the human engraftment profile. After 12 weeks of engraftment mice were injected with 1-5×10$^6$ autologous CD33-targeting CAR T cells. At the end of the experiment bone marrow and spleen were harvested to assess for lineage composition.

Colony Forming Cell (CFC) Assay.

One day after electroporation, 1000 CD34+ cells were plated in 1.1 ml of methylcellulose (MethoCult H4435 Enriched, Stem Cell Technologies) on 6 well plates in duplicate and cultured for two weeks at 37° C., 5% CO2, 95% humidity. Colonies were then counted and scored. Individual colonies were picked and lysed in 40 μl of lysis buffer containing 50 mM NaOH and 0.2 mM EDTA. Samples were heated to 95° C. for 20 minutes then cooled down, after which 1μl of 1M TrisCl was added. 2 μl of reaction was used for PCR with AccuPrime Pfx SuperMix (Invitrogen, 12344-040) as per manufacturer's instructions.

Also, MethoCult wells were solubilized with R10 media overnight and flow cytometry was performed on single-cell suspensions. Cell morphology was analyzed by Cytospin and stained with DiffQuik staining procedure.

Flow Cytometry.

The following anti-human antibodies were used to evaluate the CD34+ cells 7 days after electroporation: CD34-APC (BioLegend, 343510), CD38-BV711 (BioLegend, 303528), CD33-PE (eBioscience, 12-0339-41), CD45-BV421 (BioLegend, 304032), and Live/Dead Fixable Aqua (Life Technologies, L34957). FMO control was used for gating negative cell percentage. For MethoCult differentiated cells, CD11b-FITC (BioLegend, 301329), CD14-APC (BD, 340436) were used in addition to CD45-BV421, CD33-PE and Live/Dead Fixable Aqua as above. For mouse peripheral blood analysis, mouse CD45-APC/Cy7, human CD45-BV421, CD3-BV605, CD19-PE/Cy7, CD33-PE, CD11b-FITC, and CD14-APC were used.

DNA Analysis.

Genomic DNA was extracted from the Molm14 and CD34+ cells using the High Pure PCR Template Preparation Kit (Roche, 11796828001). PCR was performed using the following primers:

```
CD33F:
                                      SEQ ID NO: 1
5'-AGCTGCTTCCTCAGACATGC-3',.

CD33R:
                                      SEQ ID NO: 2
5'-CTGTATTTGGTACTTCCTCTCTCCA-3',.
```

Surveyor Mutation Detection kit (Transgenomics) was used to detect mutations and band intensities were analyzed using ImageJ software. PCR amplicons were analyzed by Sanger sequencing and allele modification frequency was calculated using TIDE (Tracking of In/dels by Decomposition) software.

Cytotoxicity.

CD34+ cells electroporated with either control (EMX1) or CD33-targeting gRNA were incubated at a 1:1 ratio with T cells for 72 hours. The number of T cells and CD34+ cells remaining in culture were analyzed by flow cytometry using the following antibodies: CD3-PE Cy7 (eBioscience, 24-0038-42), CD34-APC (BioLegend, 343510), CD38-BV711 (BioLegend, 303528), CD33-PE (eBioscience, 12-0339-41), CD45-BV421 (BioLegend, 304032), and Live/Dead Fixable Aqua. Countbright absolute counting beads (Invitrogen, C36950) were added to quantify the absolute numbers of cell fractions.

The results of the experiments are now described.

Example 1: Generation of CD33 Knockout (KO) HSPCs and Regeneration of Hematopoiesis A prior study of CRISPR/Cas9 mediated gene editing of human HSCs achieved 30% homozygous knockout of the CCR5 gene, demonstrating the feasibility of the approach described herein (Mandal et al. Cell Stem Cell. 2014; 15: 643-652). The prior study used plasmid nucleofection to introduce Cas9 and sgRNA into G-CSF mobilized peripheral blood CD34+ cells. The study described herein furthers the insight into gene editing in HSCs with CRISPR/Cas9 by utilizing different methods of delivery of Cas9 and gRNA into multiple sources of CD34+ cells.

As proof-of-principle, human hematopoietic stem cells with knockout of the CD33 gene (CD33 KO HSCs) were tested. CD33 is a cell surface receptor that is expressed on cells of the myeloid lineage and on most AML. It belongs to a family of sialic acid-binding, immunoglobulin-like lectins (siglecs), that recognize sialylated glycoproteins. These proteins carry immunoreceptor tyrosine-based inhibitory motifs (ITIMs) within their cytoplasmic domains, suggesting an inhibitory signaling function. The precise role of CD33 in the hematopoietic system is not well known, and it may not be essential for myeloid cell function. The functional capacities of CD33 KO HSCs were assessed to understand the impact of CD33 loss.

Figure 1B:
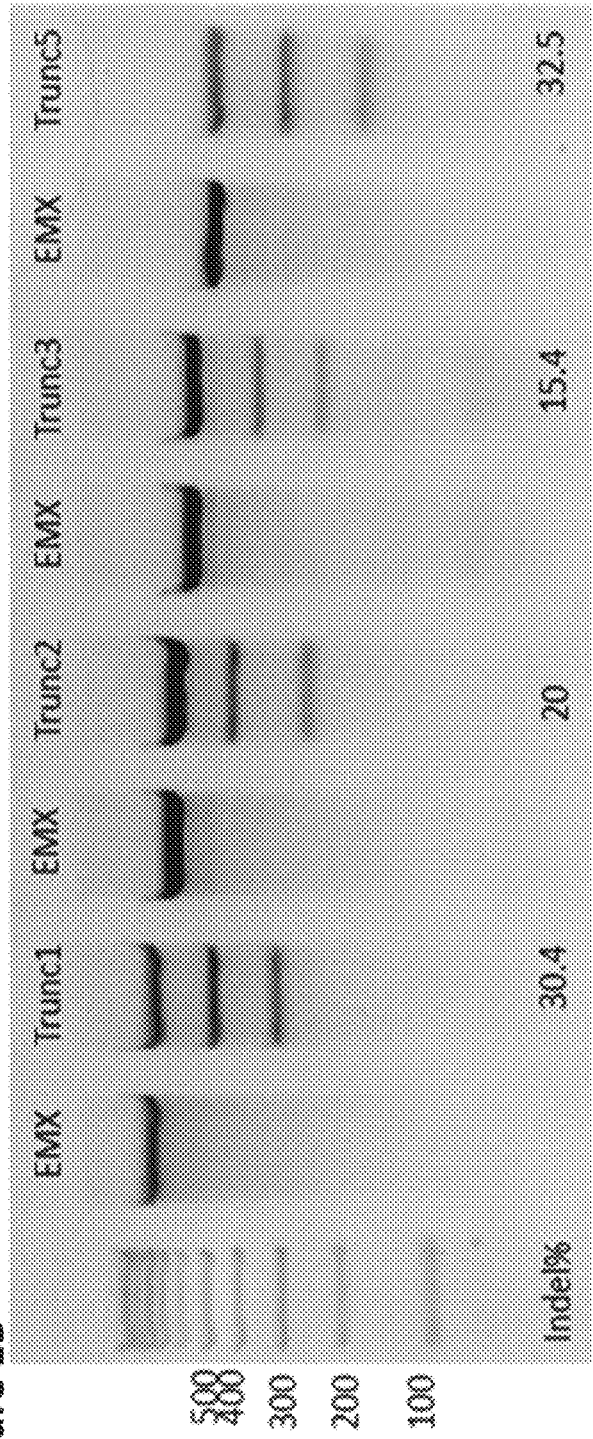

Four highly active gRNAs against CD33 identified by Doench et al, (Nat Biotechnol. 2014; 32: 1262-1267) were screened in the Molm14 cell line. To determine if CD33 CART cells would recognize and target non-CD33 expressing cells, Molm14 cells were electroporated with Cas9 mRNA on day 1 and gRNAv1-5 on day 2. gRNAv5 had the highest efficacy in generating phenotypic loss of CD33, as measured by flow cytometry and the Surveyor nuclease assay (FIGS. 1A-1B).

Figure 2A:
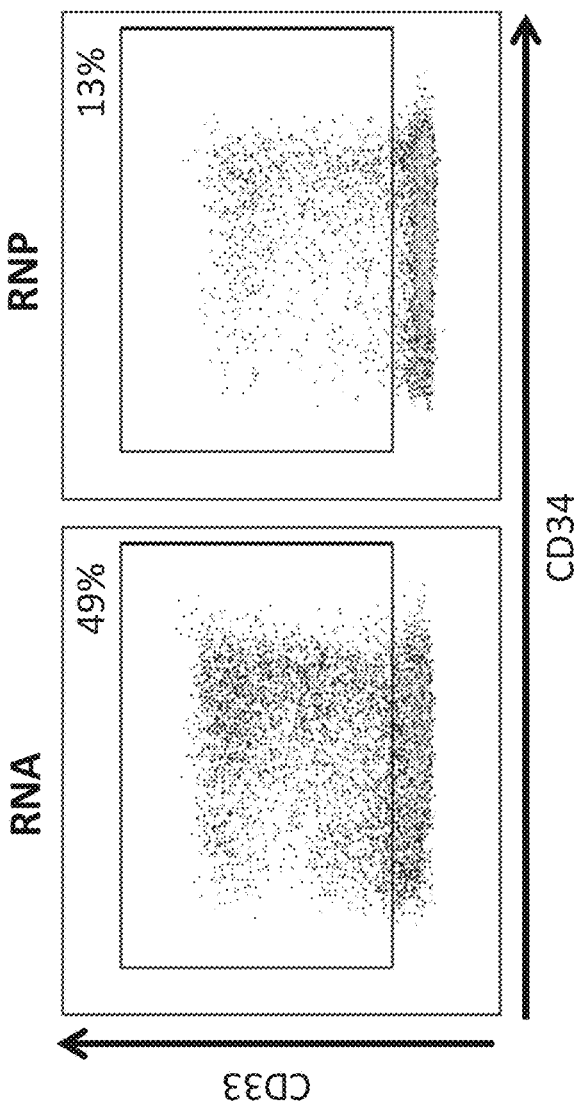
FIGS. 2A-2B are a set of plots showing CD34+ cells from mobilized peripheral blood were either electroporated twice, initially with Cas9 mRNA and subsequently with CD33-targeted gRNA, or alternatively electroporated once with Cas9 protein complexed with the same gRNA.
Figure 2B:
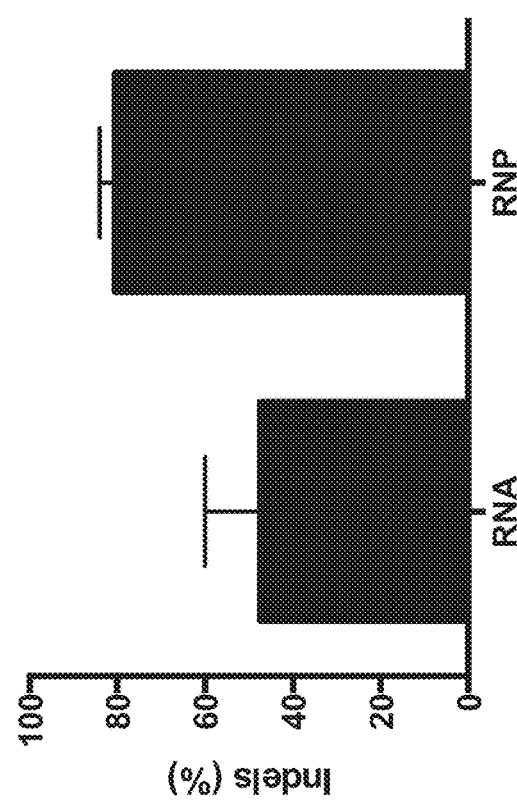

CD34+ cells from mobilized peripheral blood were either electroporated twice, initially with Cas9 mRNA and subsequently with CD33-targeted gRNA, or alternatively electroporated once with Cas9 protein complexed with the same gRNA. FIG. 2A shows a representative plot of CD33 expression by flow cytometry 7 days after electroporation. FIG. 2B is a graph showing indel frequencies measured by TIDE analysis of PCR amplicons spanning the gRNA target site, averaged for different donors; n=4 for RNA and n=2 for RNP.

Figure 3A:
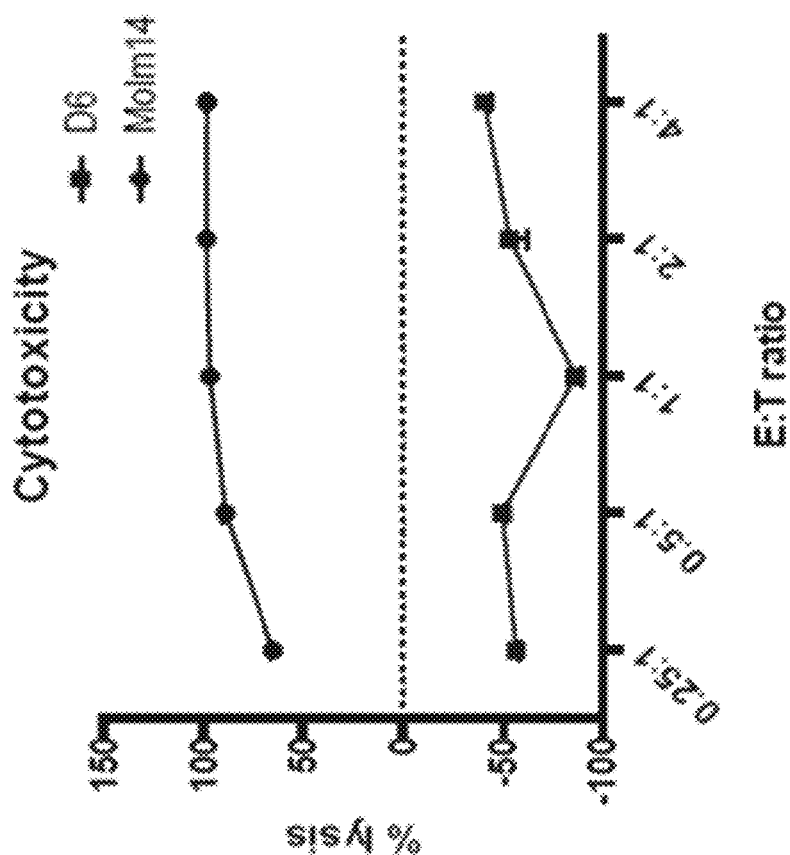
FIGS. 3A-3B are a set of graphs showing that CART33 cells do not target CD33 negative cells.
Figure 3B:
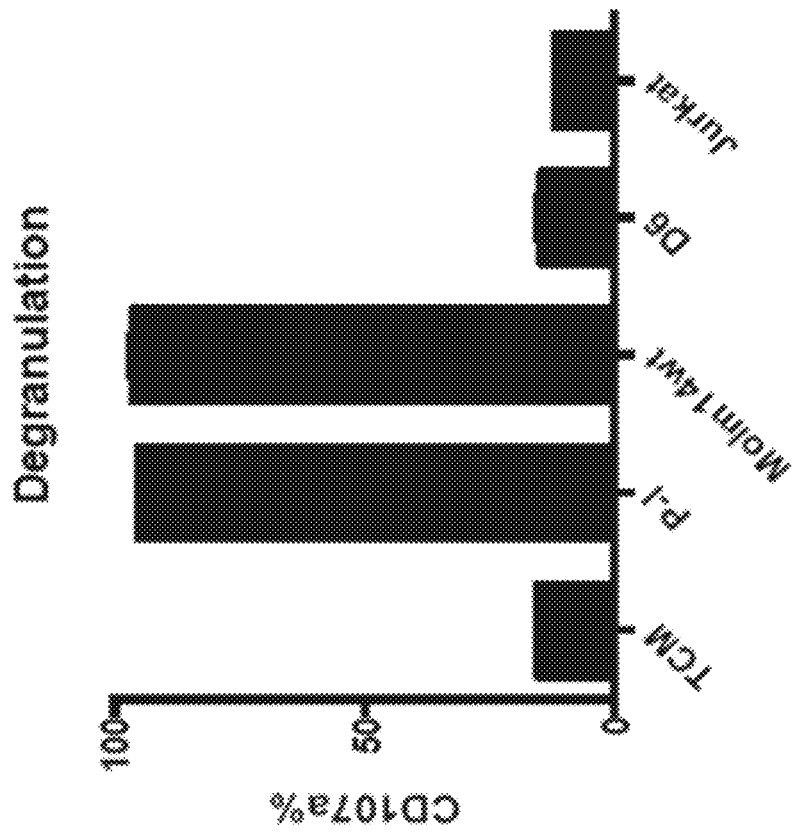

CD33 positive (D6 and Jurkat cells) and negative cells (Molm14 cells) were co-cultured with CD33 CART cells. FIGS. 3A-3B show that CD33 selectively targeted CD33 positive cells, while CD33 negative cells did not display degranulation or lysis.

This gRNA was used to generate CD33 knockout (KO) HSCs from G-CSF mobilized peripheral blood (mPB) CD34+ cells using RNA electroporation of Cas9 mRNA and gRNA (FIGS. 4A-4D). The CD33 KO HSCs demonstrated loss of CD33 expression. Using cells from four donors, the method generated 30-60% edited cells, with 30-50% viability.

Figure 4B:
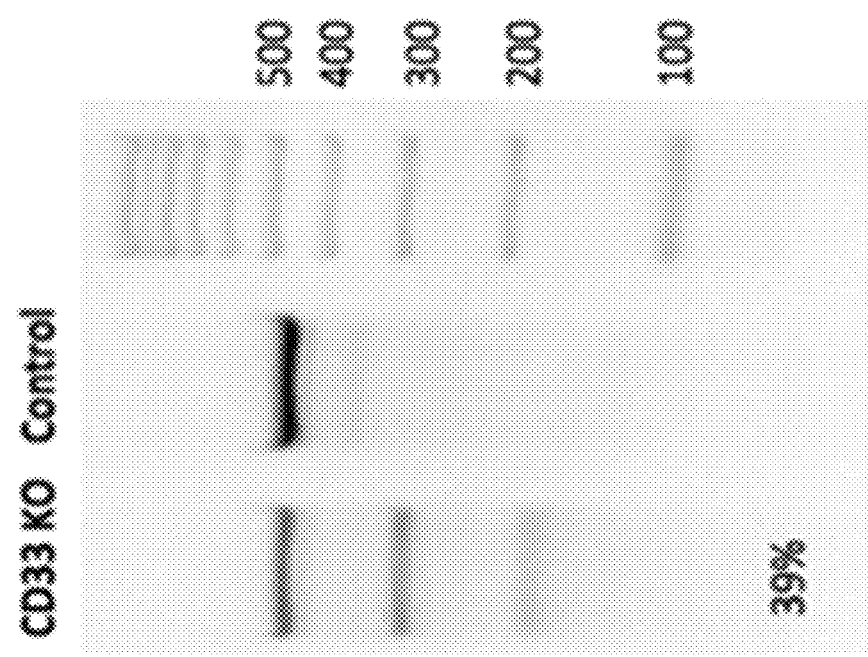
FIGS. 4A-4D are a panel of images showing CD33 KO in human CD34+ cells.
Figure 4A:
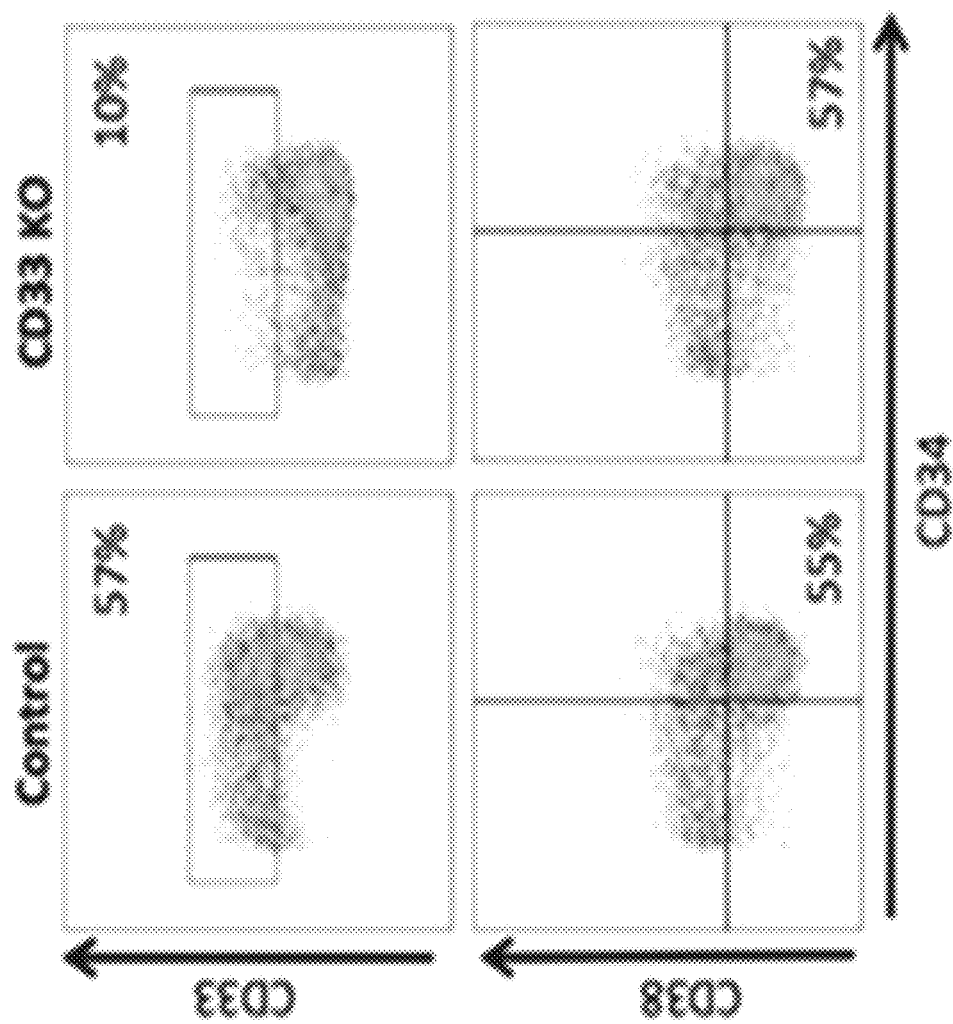
Figure 4C:
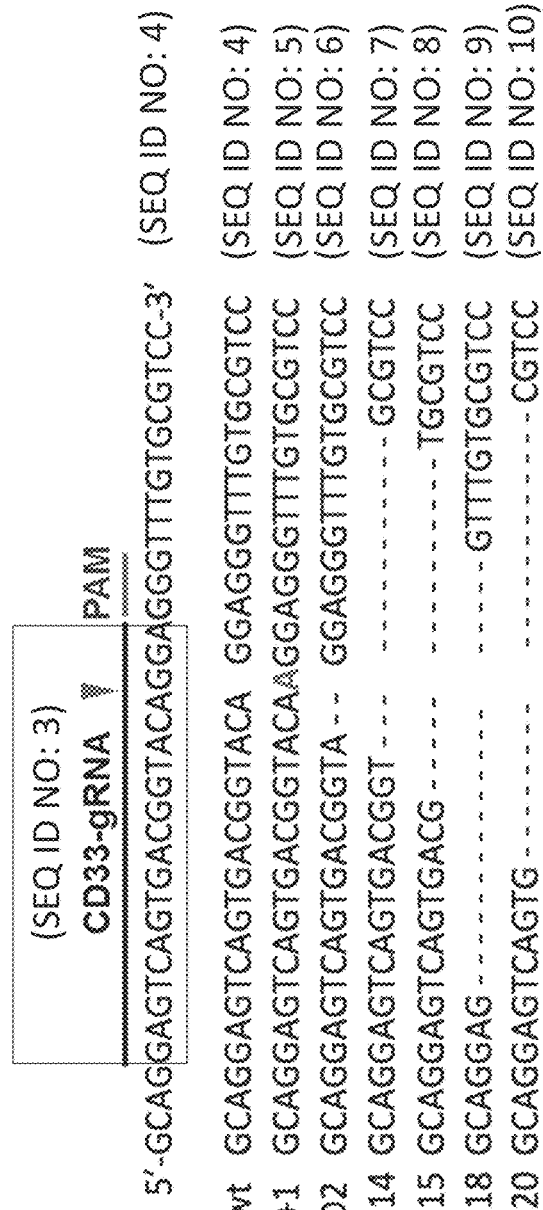

Sanger sequencing of CD33 KO HSC colonies revealed that a large proportion of mutant clones carried a single A nucleotide insertion (+A mutation) at the Cas9 cut site (FIG. 4C). This frameshift mutant generated a stop codon early in the CD33 protein coding sequence, thus ensuring that CD33 was not expressed. There are reports that adding a homology-directed repair (HDR) template to Cas9/gRNA can increase the frequency of mutations, likely because it provides an alternative repair template, rather than the intact sister chromosome. Therefore, a single-strand DNA oligonucleotide HDR repair template with a +A mutation was added to the most efficacious electroporation method, with the goal of further increasing the number of CD33 KO HSCs.

Figure 4D:
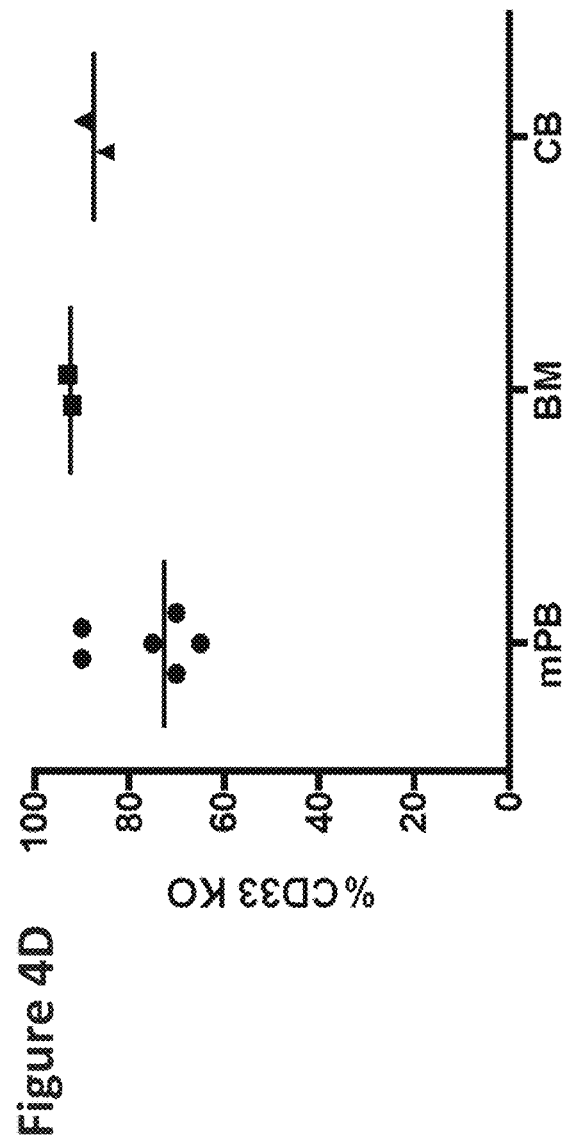

In the clinical setting, different sources of CD34+ cells (mPB, cord blood, and bone marrow) need to be utilized based on the availability of HLA-matched donors. Each source has unique characteristics, and the efficacy of CRISPR-mediated gene editing varies based on the source. The efficacy of generating CD33 KO HSCs when using different sources of CD34+ cells was compared. The protocol of the current invention used herein generated a high percentage of CD33 KO in CD34+ cells regardless of the source (FIG. 4D).

CD33 KO HSCs were generated with up to 60% efficacy using RNA electroporation. The limitation of this method is the viability of the cells after two electroporations, which requires a large starting population to obtain sufficient number of cells for in vivo engraftment experiments. Instead, a single electroporation with Cas9 protein complexed with the same gRNA was used to generate high efficiency electroporation with increased cell viability (FIGS. 2A-2B).

Figure 5A:
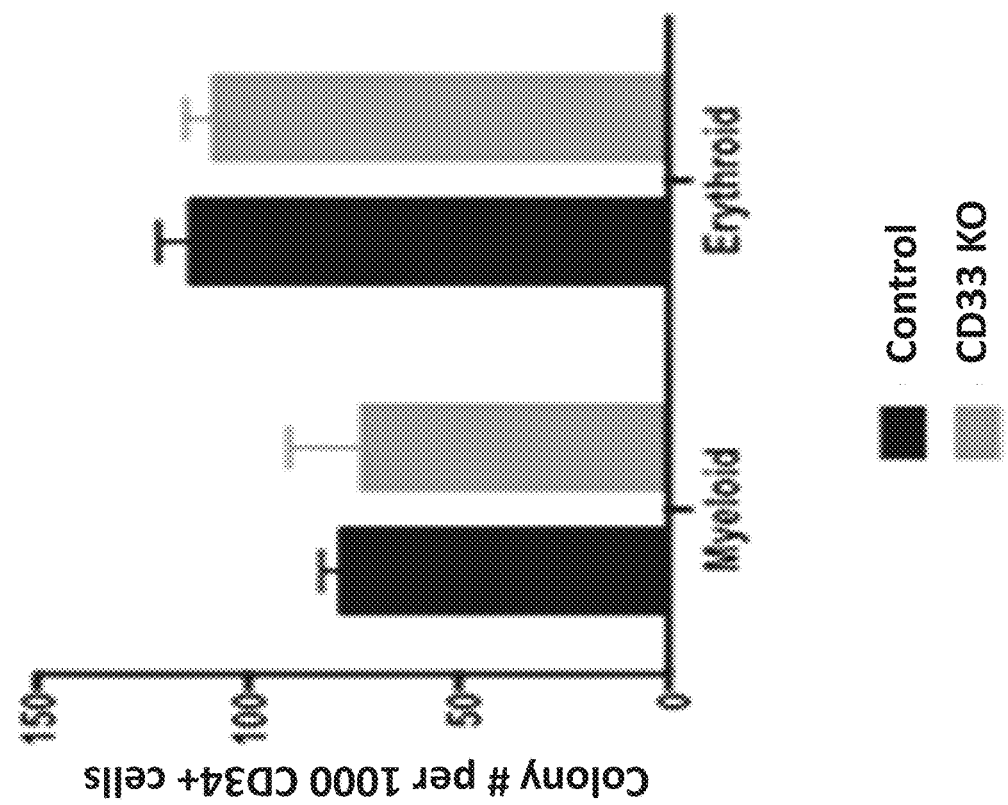
FIGS. 5A-5C are a series of plots and images showing that KO of CD33 in HSCs does not impair their normal growth and differentiation. After undergoing CRISPR of the EMX1 locus (control) or the CD33 locus, CD34+ cells were cultured in serum-free media with SCF, Flt3L, TPO, and IL-6 for 7 days, or alternatively plated on semi-solid methylcellulose media (Methocult) directly after electroporation.
Figure 5B:
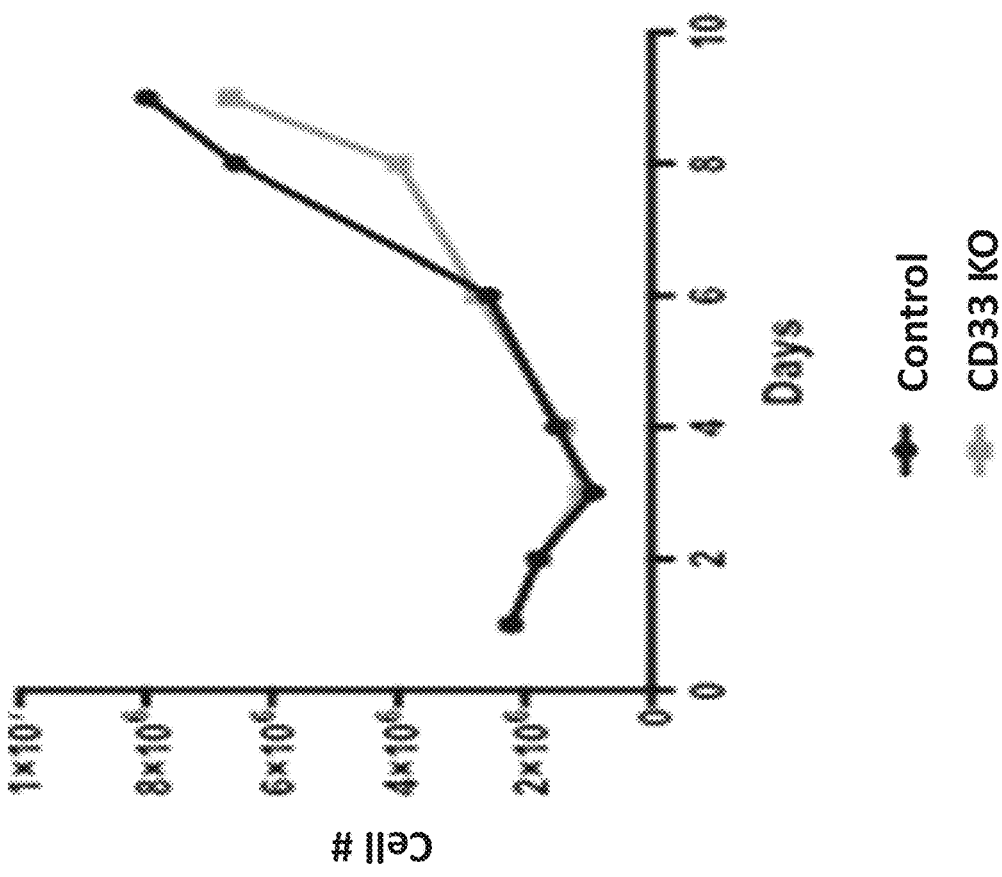
Figure 5C:
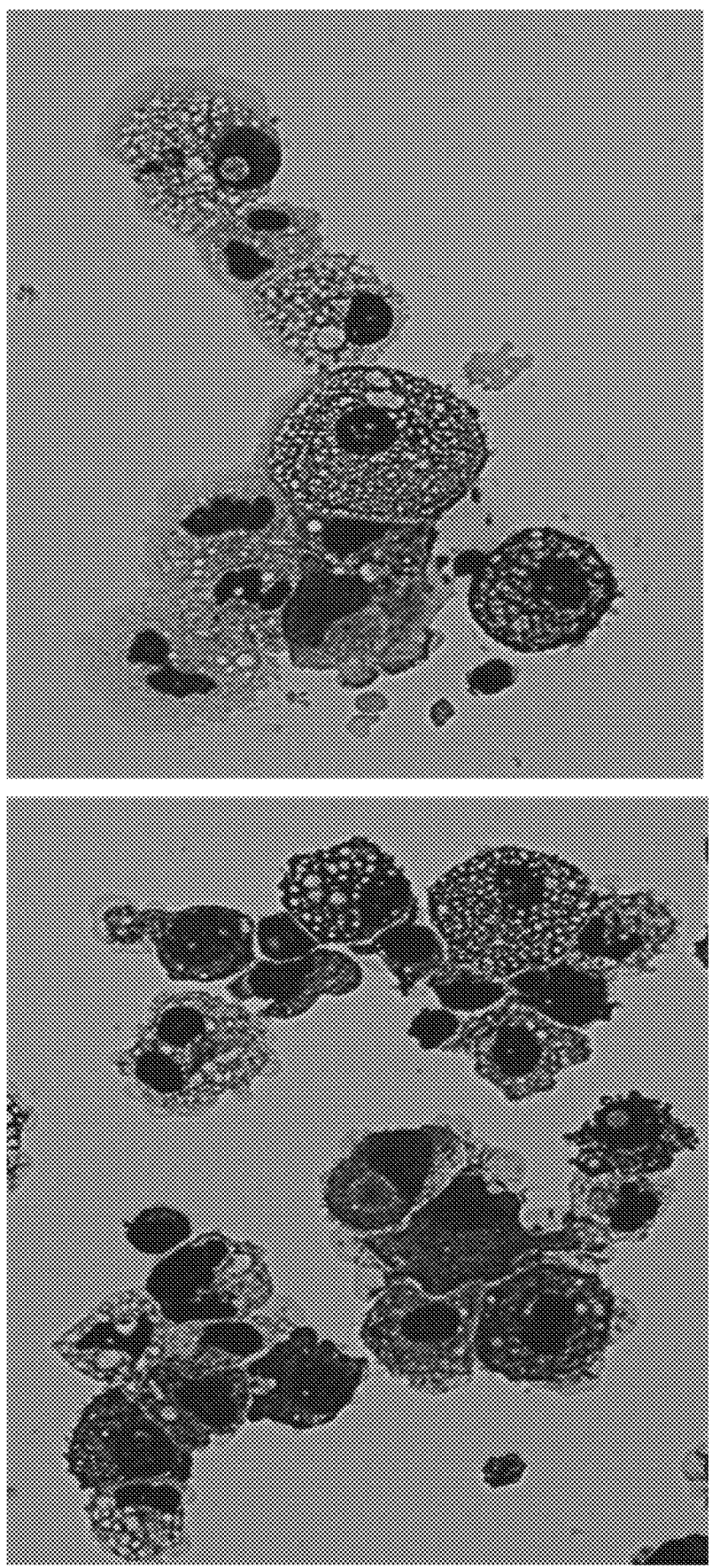
Figure 6:
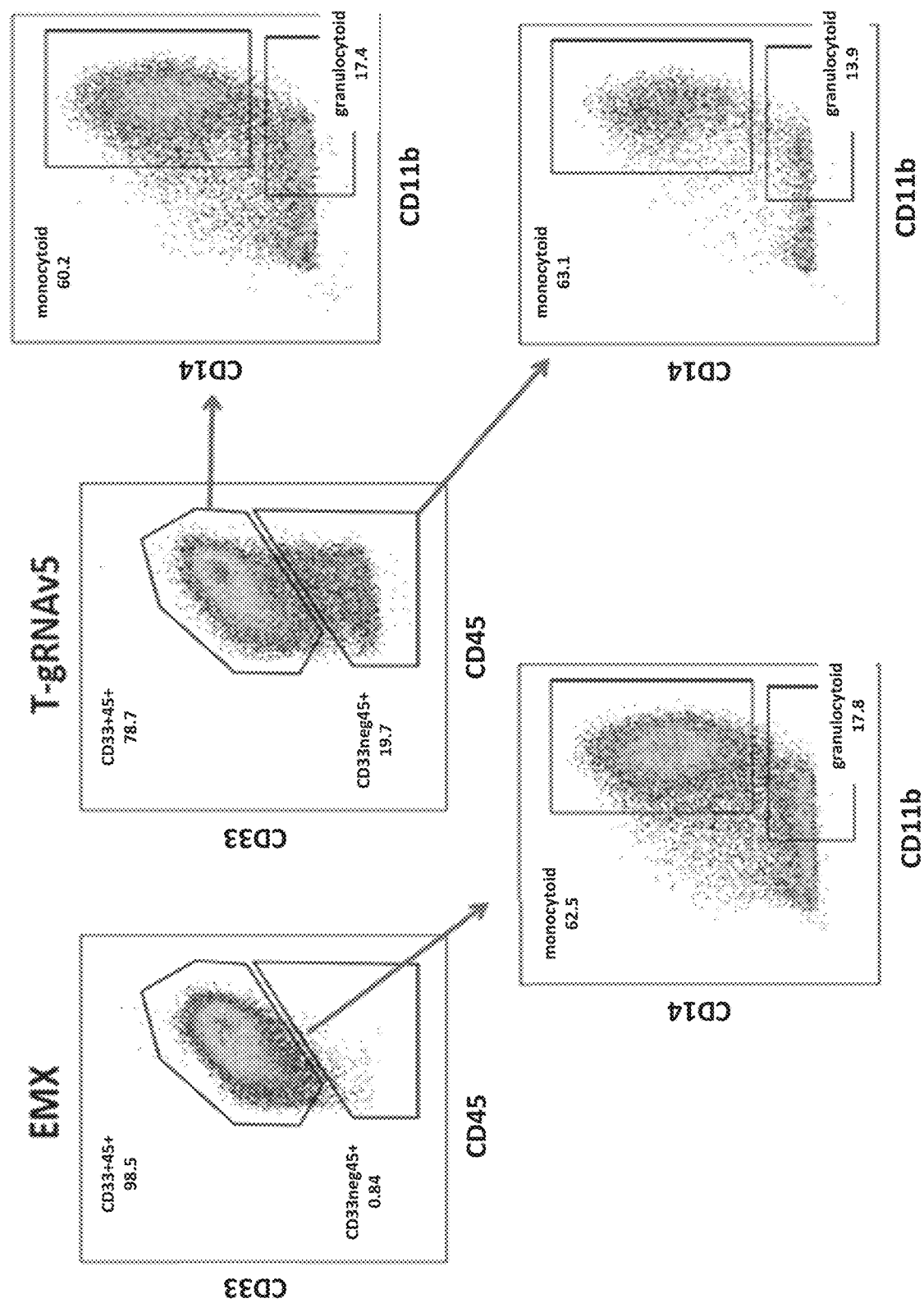
FIG. 6 is a panel of graphs of immunophenotyping of CD33 KO HSC methylcellulose colonies and CD33+ HSC methylcellulose colonies, showing identical monocytic and granulocytic differentiation in control HSC-derived colonies, CD33KO HSC-derived colonies, and in the residual CD33-expressing colonies from CD33KO HSC.

To date, no evidence has been found that CD33 KO HSCs are deficient in any way compared to control HSCs. As a control, cells were electroporated with a gRNA targeting EMX1, a gene encoding a transcription factor involved in brain development. Both EMX1 and CD33 KO HSCs grew at similar rates in culture (FIG. 5A), and methylcellulose colony-forming assay showed equivalent numbers of both myeloid and erythroid colonies (FIGS. 5B and 6). Cytospins of the CD33 KO cells showed normal morphology of neutrophil and macrophage cells (FIG. 5C)

Figure 7A:
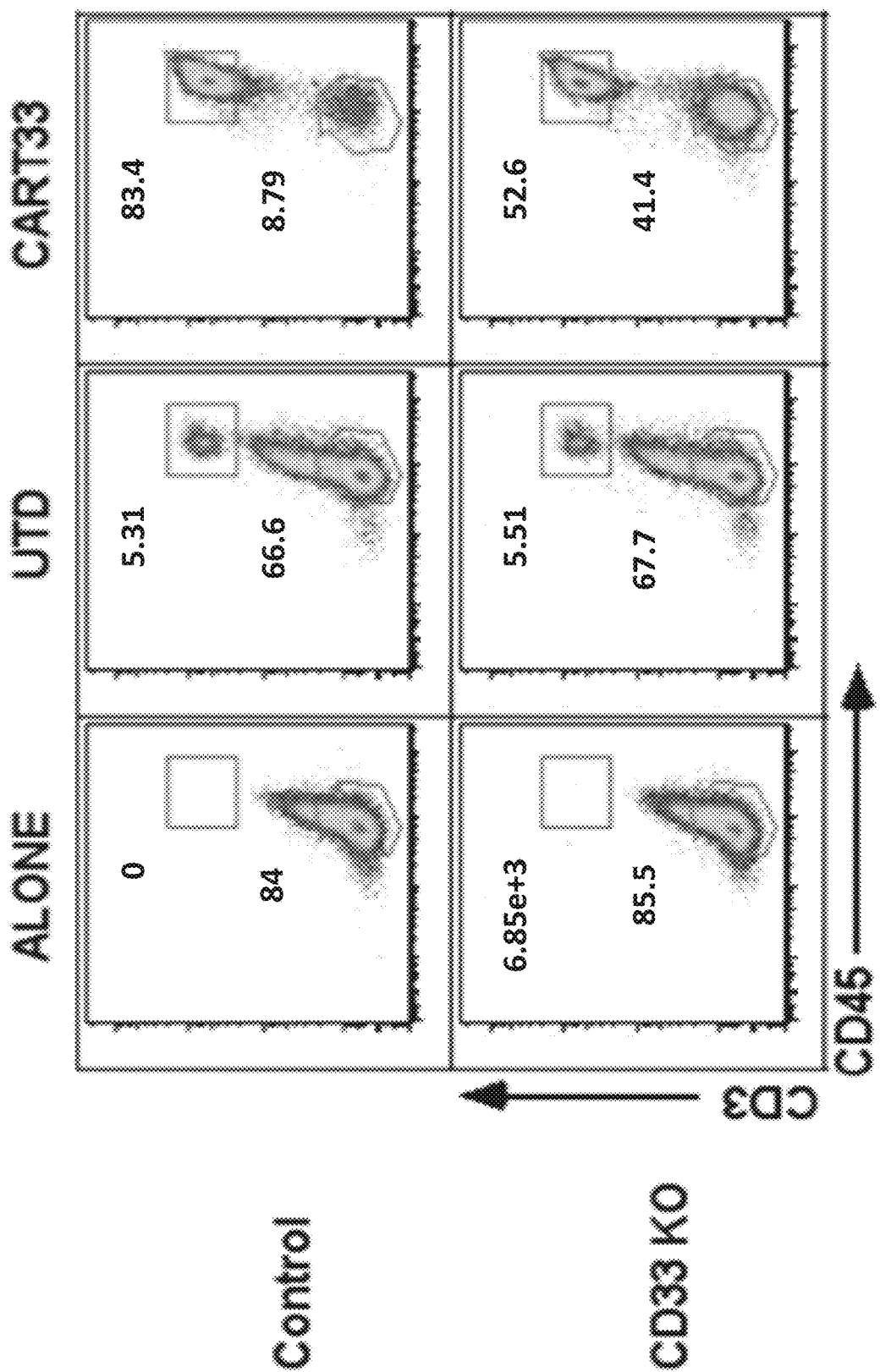
FIGS. 7A-7B are a panel of graphs showing analysis of CD33 KO HSCs co-cultured with CART33 cells.
Figure 7B:
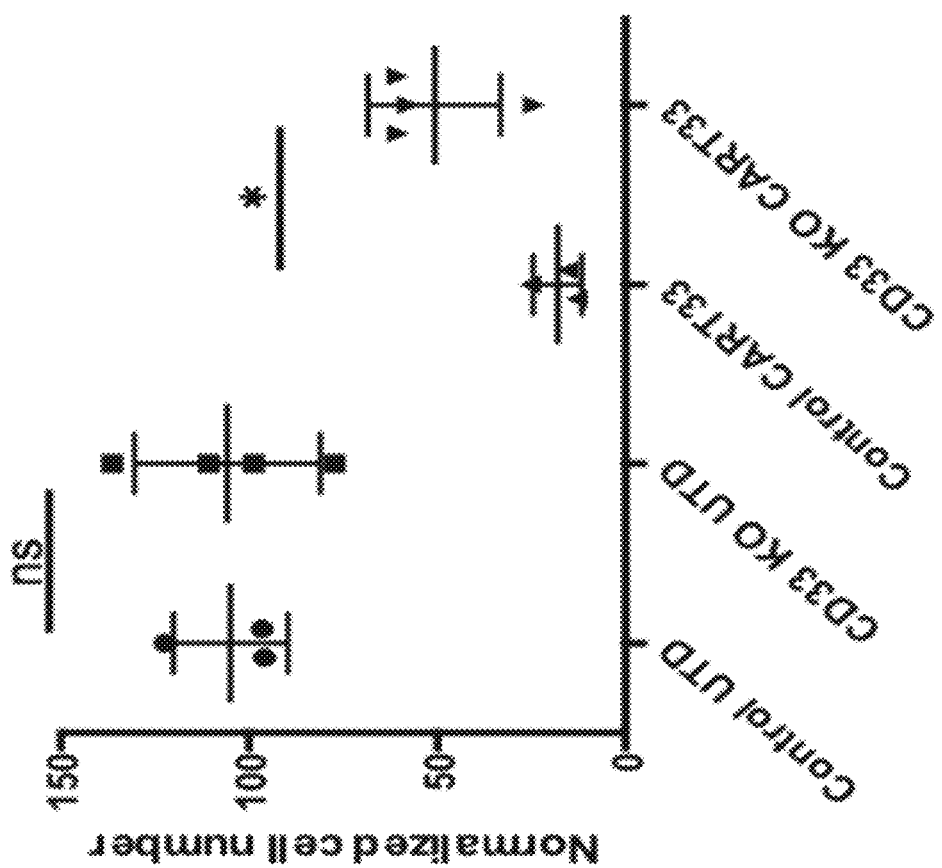

Analysis of CD33 KO HSCs showed that the cells had comparable CD3 and CD45 expression as control HSCs (FIG. 7A). When control HSCs were incubated with CART33 in vitro there was a marked decrease in cell count due to CART33-mediated killing of CD33 positive cell population, which was the majority of cells after several days of in vitro culture. In contrast, CD33 KO HSCs had a significant number of residual cells remaining after CART33 treatment (FIG. 7B).

Figure 8:
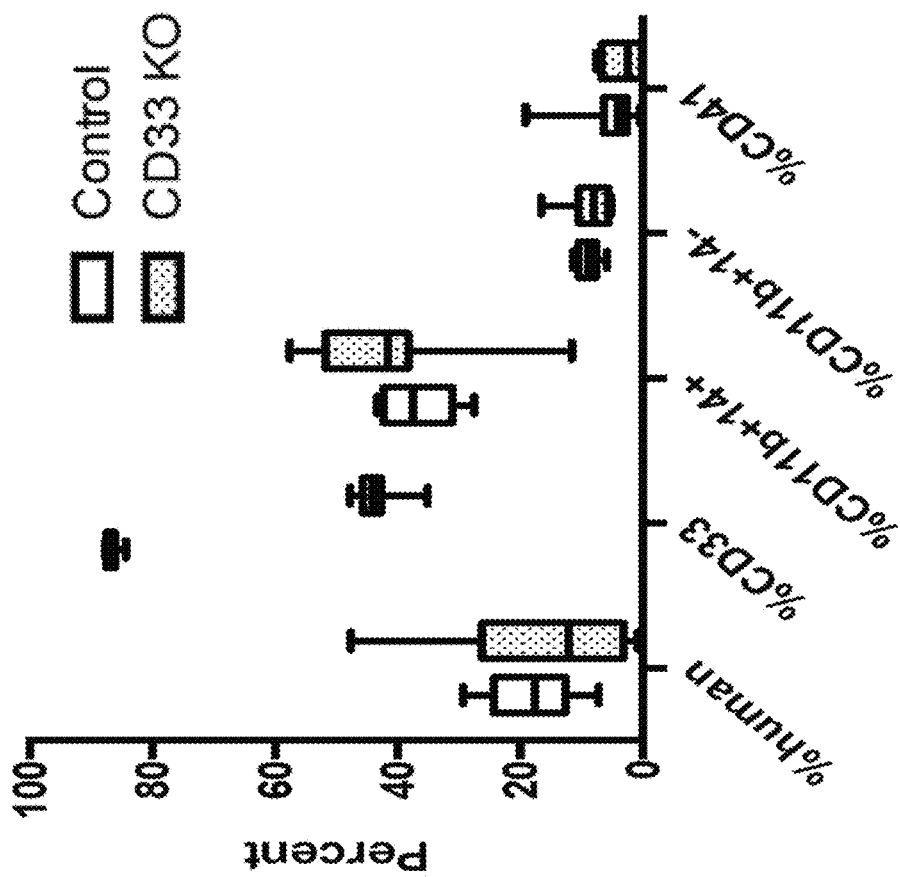
FIG. 8 is a graph showing that mice engrafted with either EMX1 or CD33 KO HSCs exhibited normal myeloid development.

More detailed functional evaluation of CD33 KO HSCs was performed in comparison with control KO HSC. NSG mice were engrafted with either EMX1 or CD33 KO HSCs. The mice engrafted with either EMX1 or CD33 KO HSCs showed normal myeloid development. The CD33 KO HSCs differentiated into mature myeloid cells (neutrophils and macrophages). Cell morphology was analyzed by cytospin and characteristic cell surface markers (CD11b, CD15, CD14, CD16, CD45, CD66b, and HLA-DR) by flow cytometry (FIG. 8).

Figure 9A:
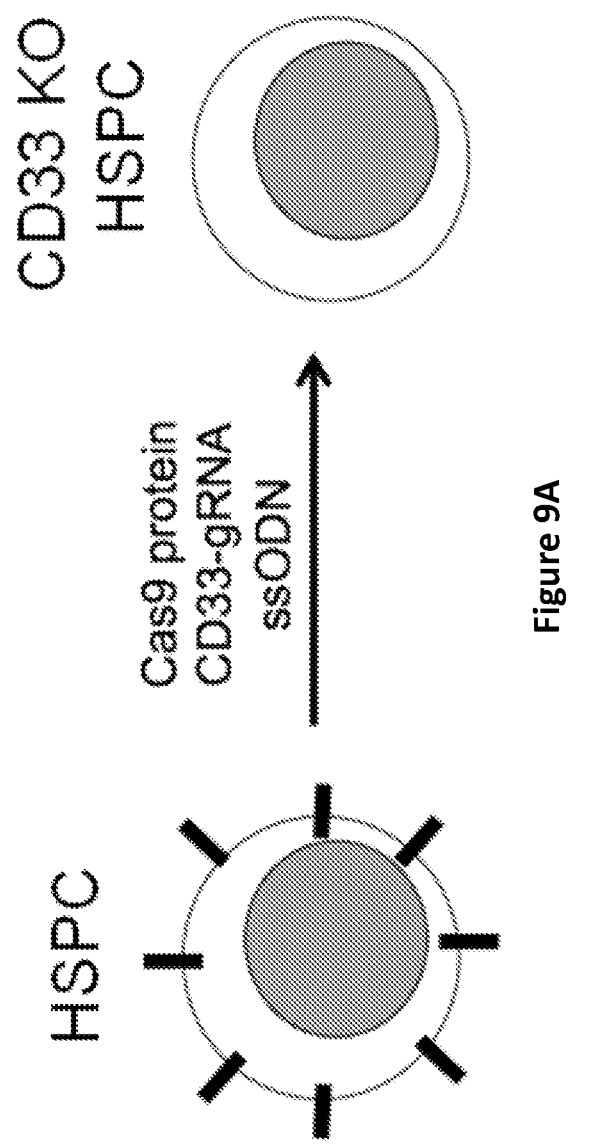
FIGS. 9A-9J are a series of plots and images showing that CD33 KO human CD34+ cells are capable of long-term multi-lineage engraftment.
Figure 9B:
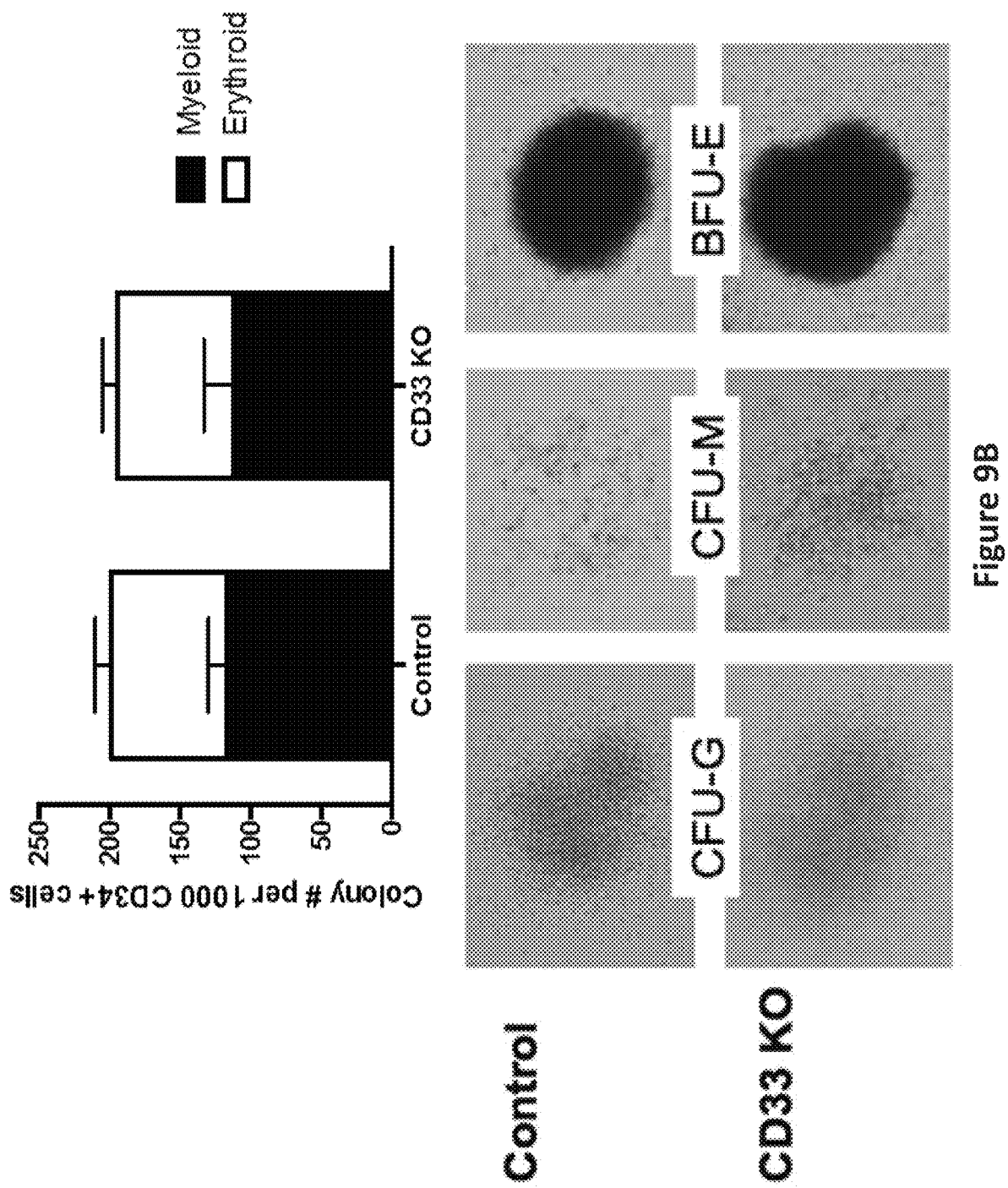
Figure 9C:
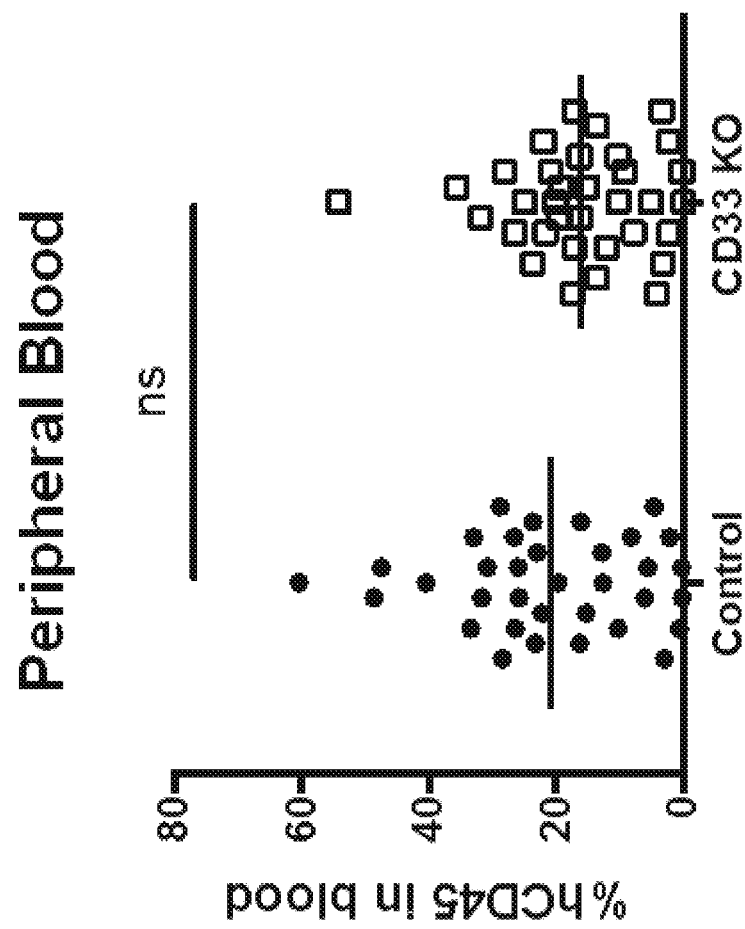
Figure 9D:
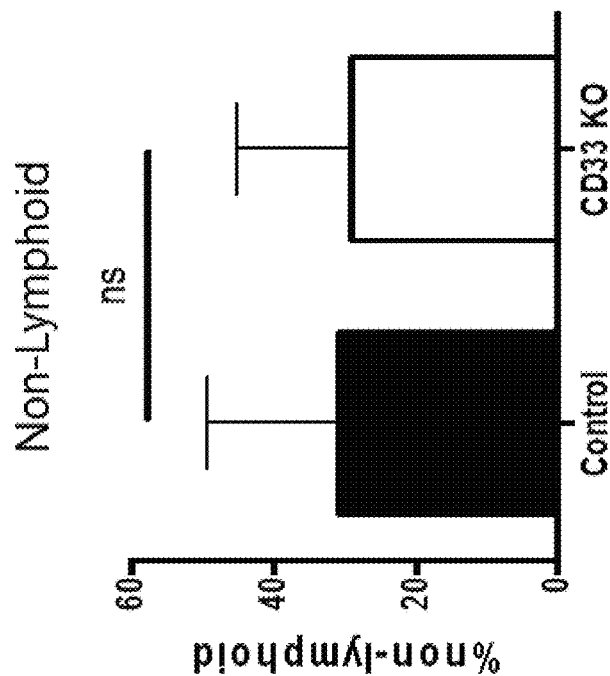
Figure 9D:
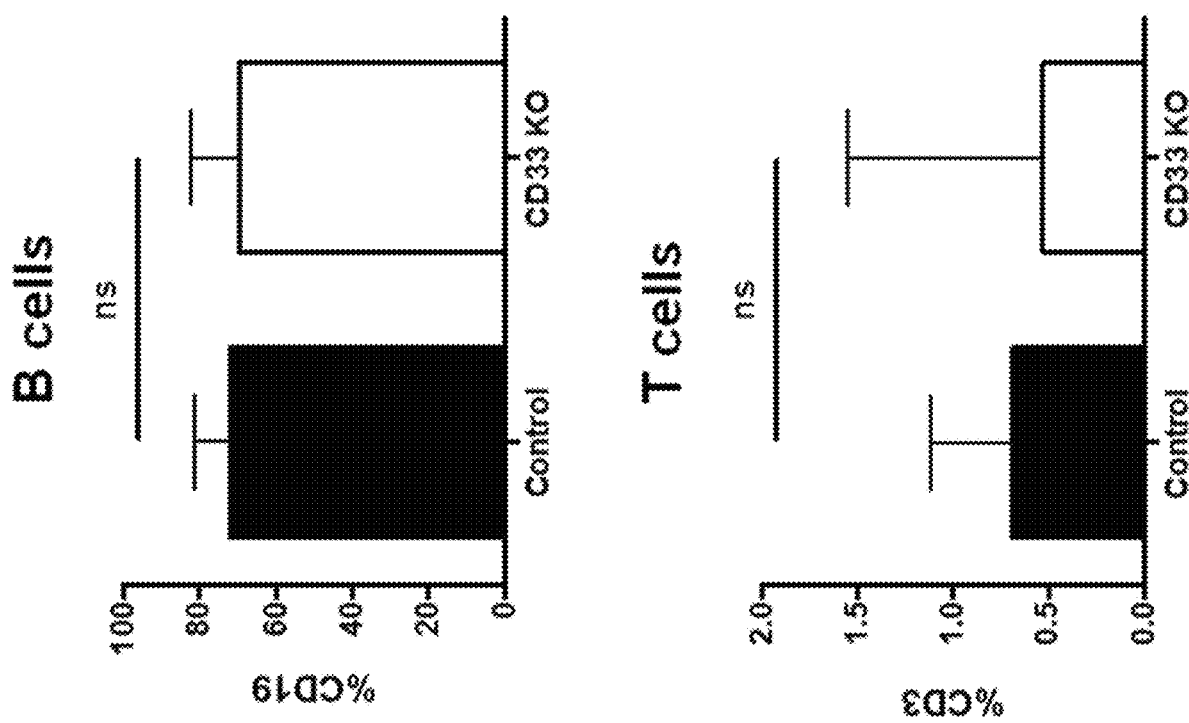
Figure 9E:
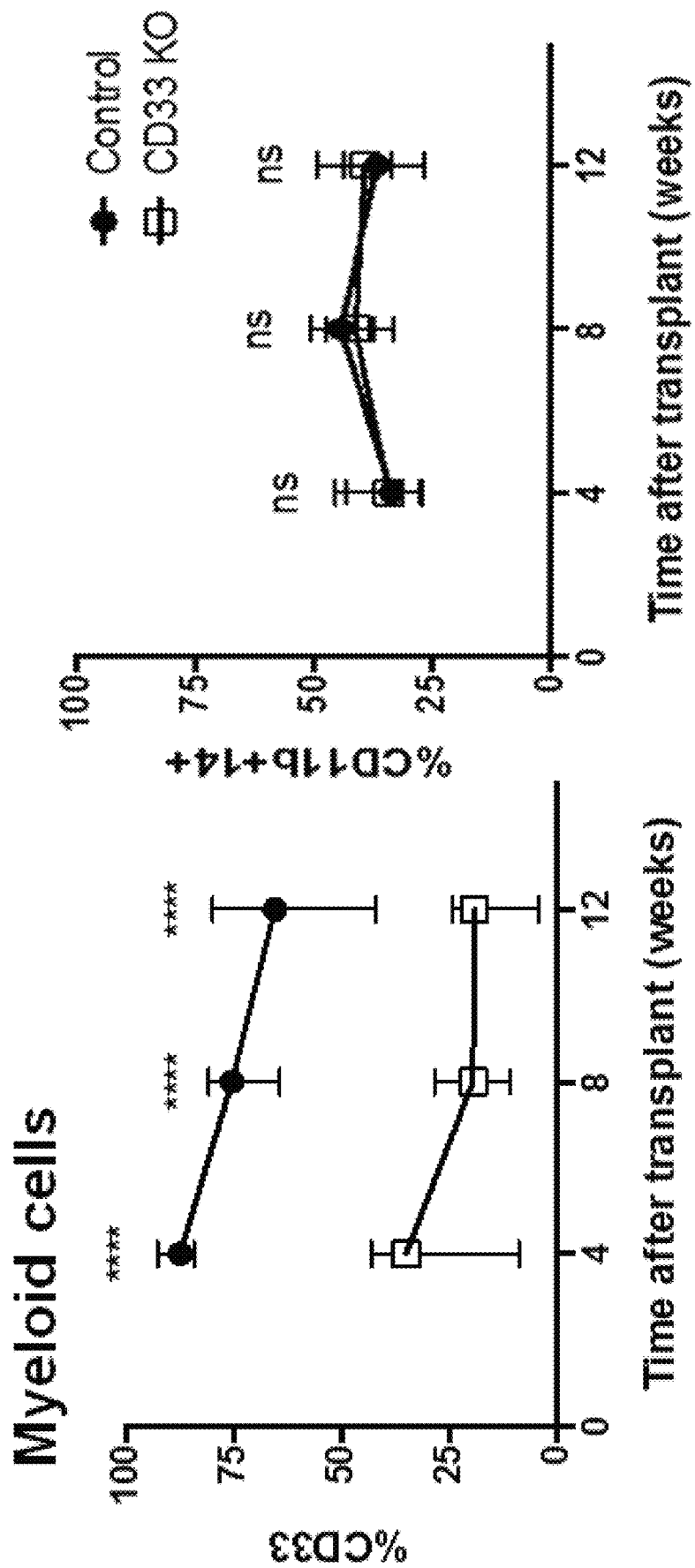
Figure 9F:
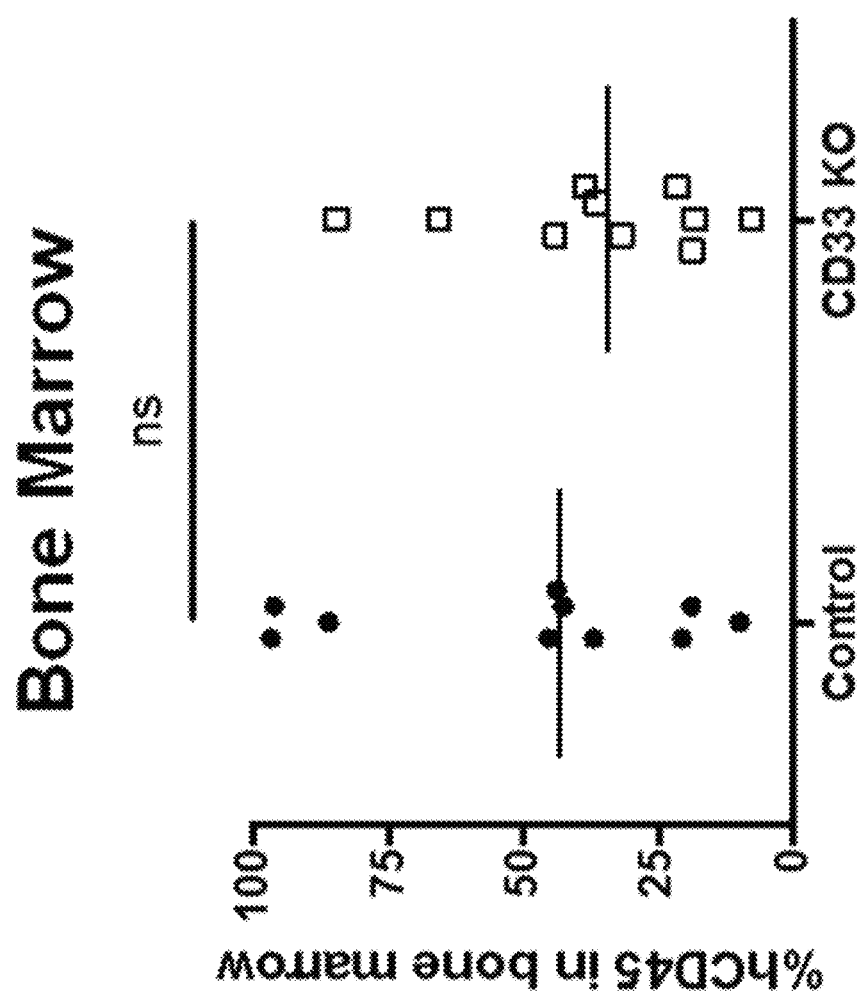
Figure 9G:
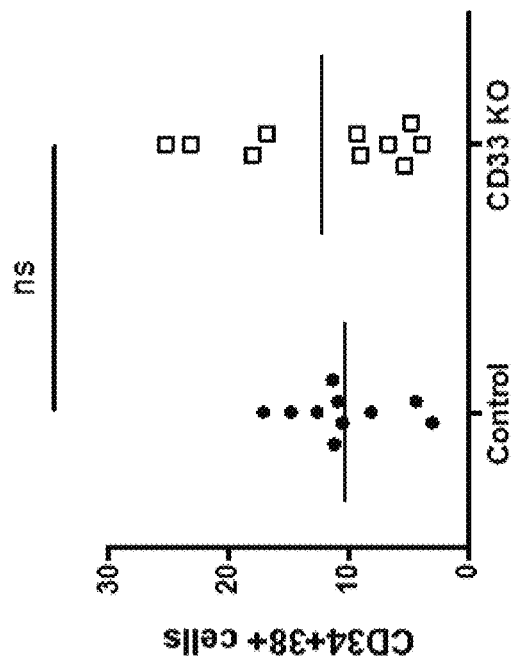
Figure 9H:
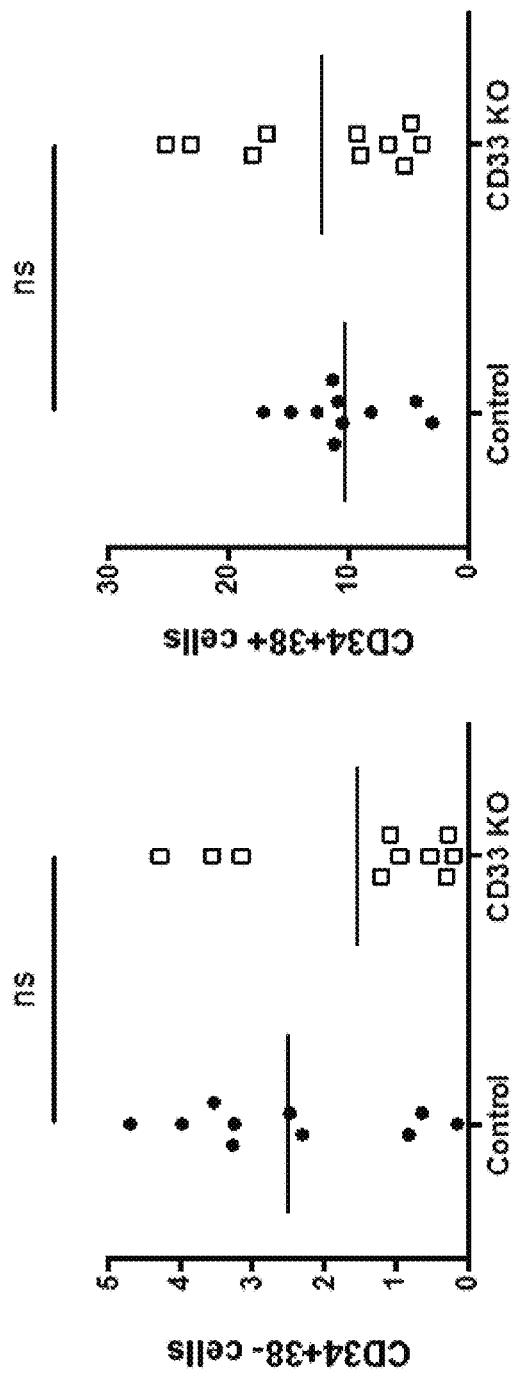
Figure 9I:
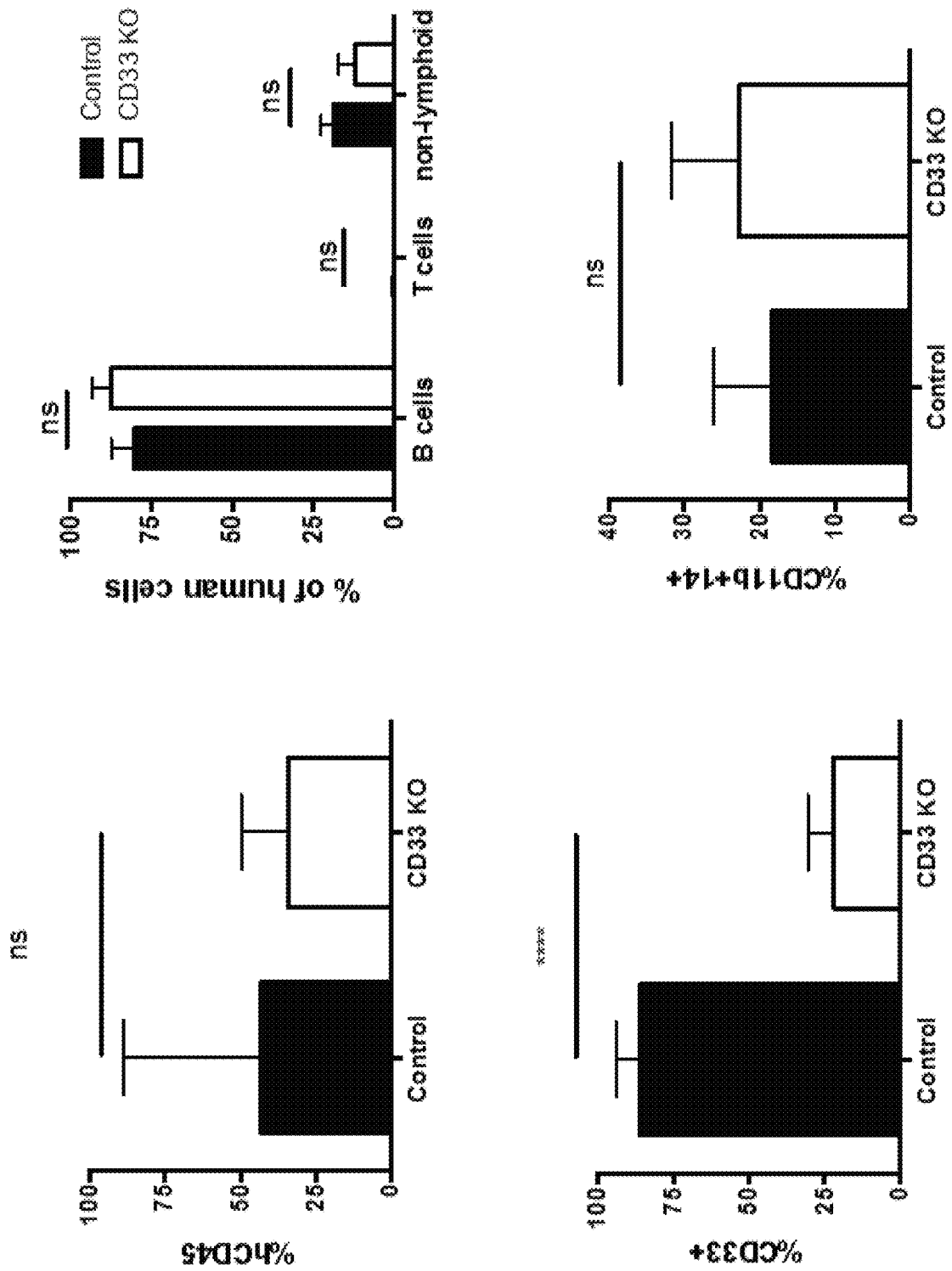
Figure 9J:
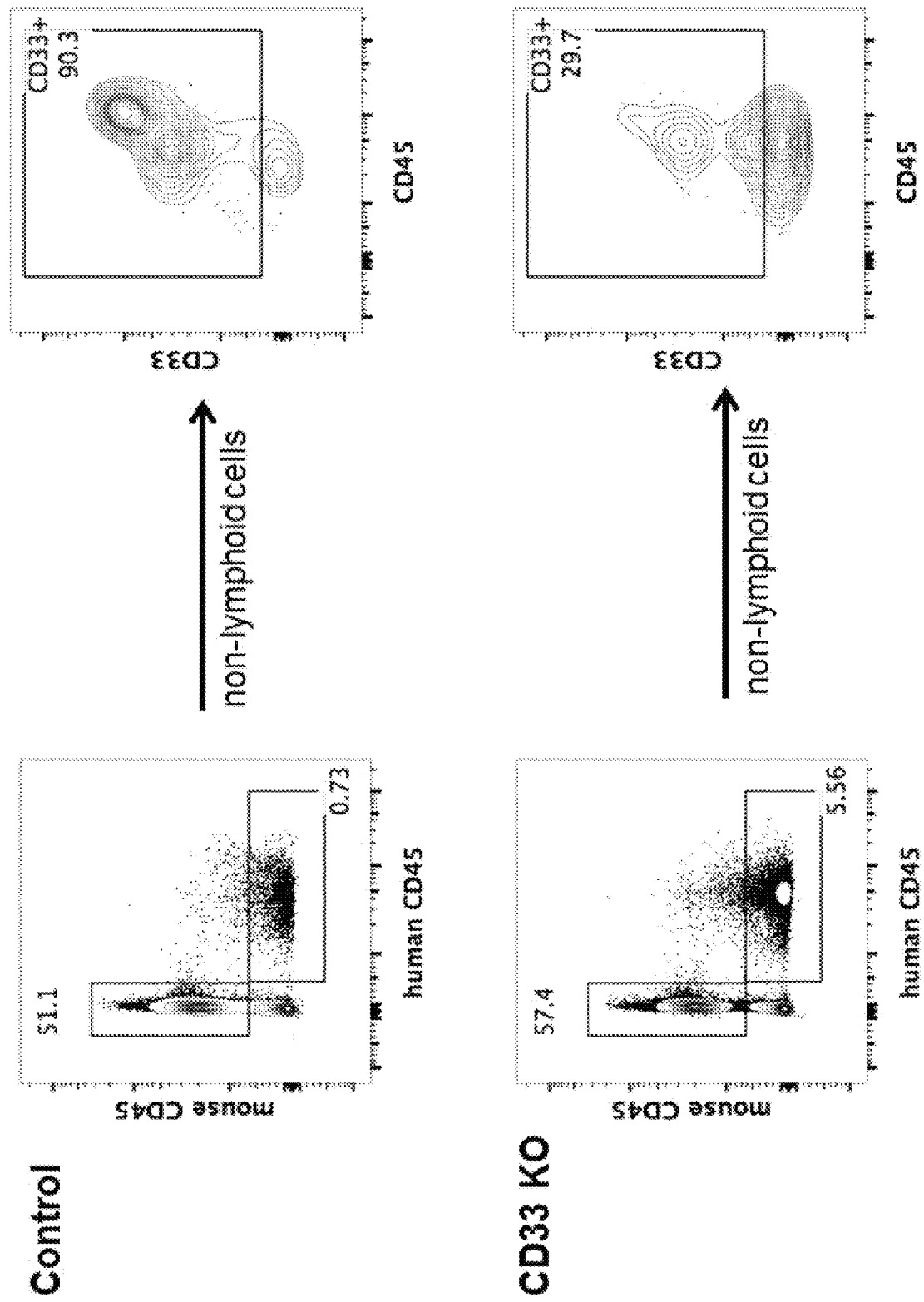

CD33 KO human CD34+ cells were capable of long-term multi-lineage engraftment (FIGS. 9A-9H). Primary human CD34+ cells were derived from G-CSF mobilized peripheral blood (FIG. 9A) and led to equivalent number and morphology of hematopoietic myeloid and erythroid colonies (FIG. 9B). 8-12 week old NSG mice were injected with either control or CD33-KO CD34+ cells. Twelve weeks later, the percentage of hCD45 in peripheral blood (engraftment) was measured (FIG. 9C). B cells (CD19+), CD3+ T cells (CD3+), and non-lymphoid cells were detected with no significant difference between the two groups (FIG. 9D). Human myeloid cells in CD33 KO HSPC-engrafted mice had significantly reduced levels of CD33 expression, but no difference was observed in CD11b+14+ expression compared to control HSPC-engrafted mice (FIGS. 9E and 9I). In addition, bone marrow harvested after 16 weeks showed equal levels of human CD45+ engraftment in control and CD33 KO HSPC-engrafted mice (FIG. 9F). There were no significant differences in the levels of human stem cells and myeloid progenitors in the bone marrow of mice engrafted with either control or CD33 KO HSPCs (FIG. 9G). Bone marrow was harvested from NSG mice after 16 weeks of primary engraftment then transferred into secondary recipients and analyzed after 12 additional weeks. Sustained human engraftment with persistent CD33 KO phenotype was observed (FIG. 9H). In the bone marrow, no difference in total human engraftment between the CD33KO or CD33WT groups was observed (FIG. 9I, top left), with differentiation into lymphoid and myeloid lineages (FIG. 9I, top right), with the exception of decreased CD33 expression (FIG. 9I, bottom left). Myeloid cells from CD33KO had expression of CD11b and CD14 at levels comparable to controls (FIG. 9I, bottom right). At the end of the 16 week primary transplant, expression of CD33 on non-lymphoid human cells indicated protracted, stable absence of CD33 in marrows of xenografted mice (FIG. 9J).

Example 2: CD33 KO HSPCs are Resistant to CD33-Targeted Therapy

Figure 10A:
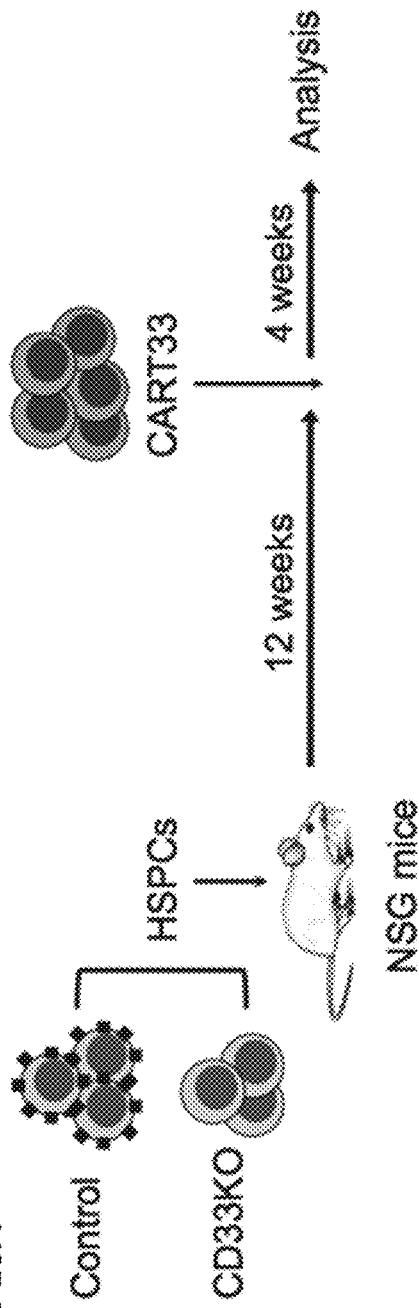
FIGS. 10A-10D are a series of plots and images showing CD33 KO HSPCs are resistant to CART33.
Figure 10B:
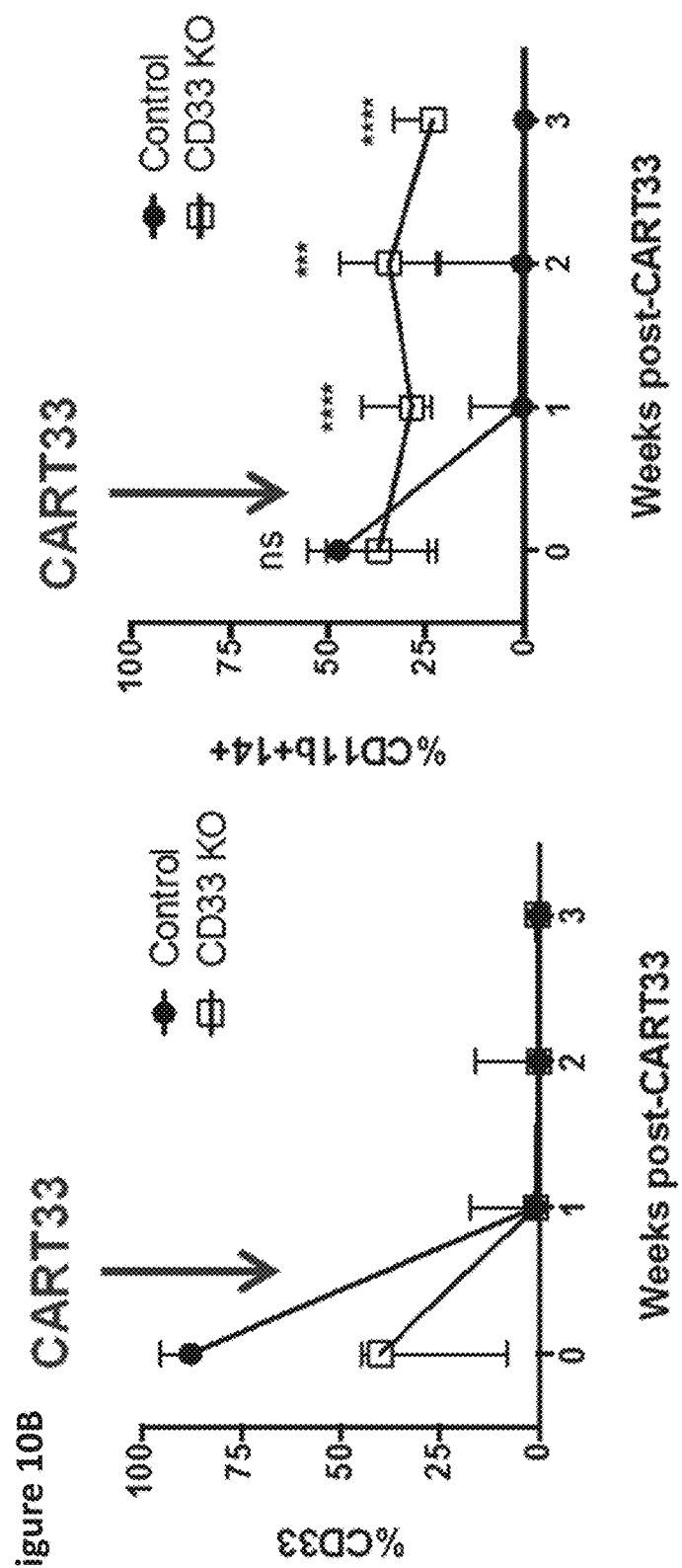
Figure 10C:
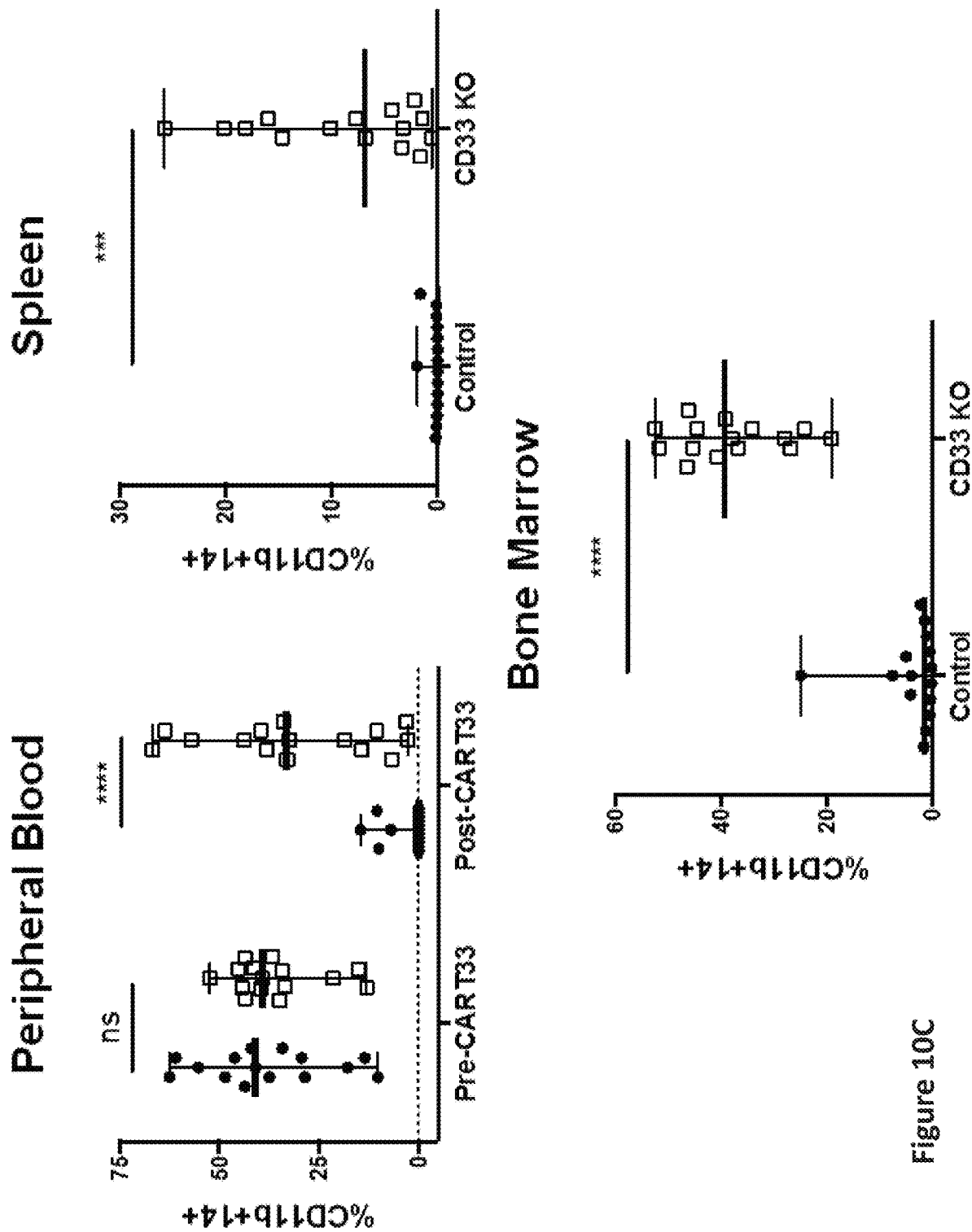
Figure 10D:
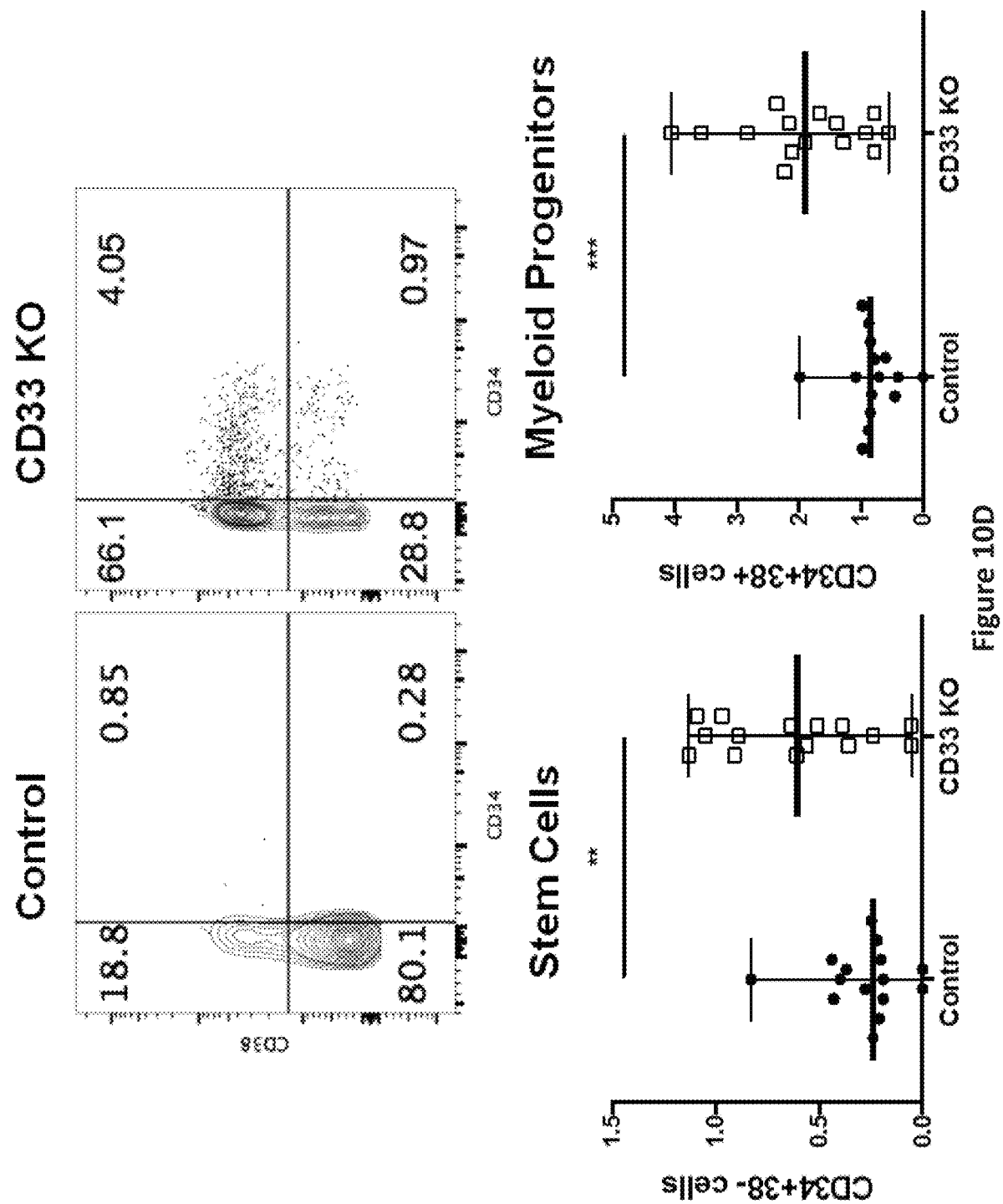

NSG mice engrafted with control or CD33 KO HSPCs were given autologous CART33 cells, and residual human myeloid cells were assessed after 4 weeks (FIG. 10A). CD33 was eliminated in the peripheral blood of mice treated with CART33, which leads to ablation of myeloid cells (CD11b14+) in the control HSPC-engrafted mice, while in the CD33 KO HSPC-engrafted mice the myeloid cells were sustained (FIG. 10B). Myeloid cells were detected in the peripheral blood, spleen, and bone marrow of the CD33 KO HSPC-engrafted mice after CART33 treatment, in contrast to the myeloablation seen in control HSPC-engrafted mice (FIG. 10C). Human progenitor cells were significantly increased in CD33 KO HSPC-engrafted mice after CART33 treatment compared to controls (FIG. 10D).

Figure 11A:
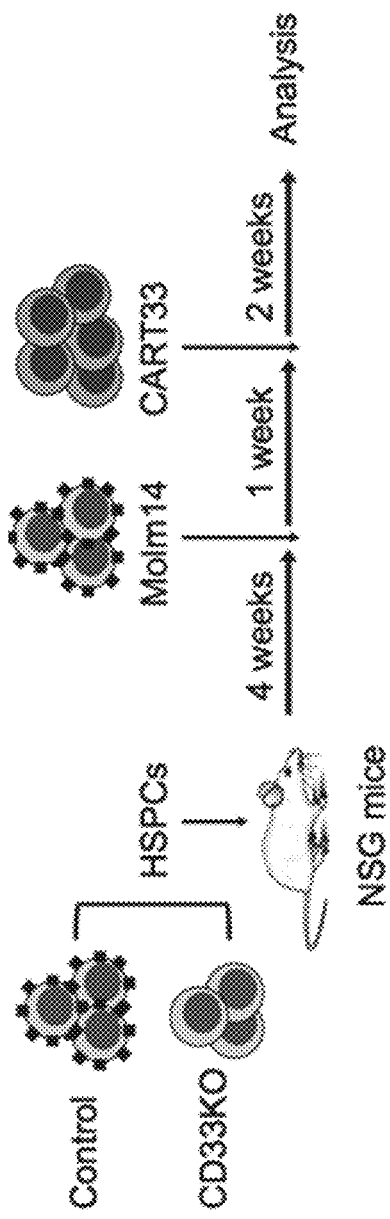
Figure 11B:
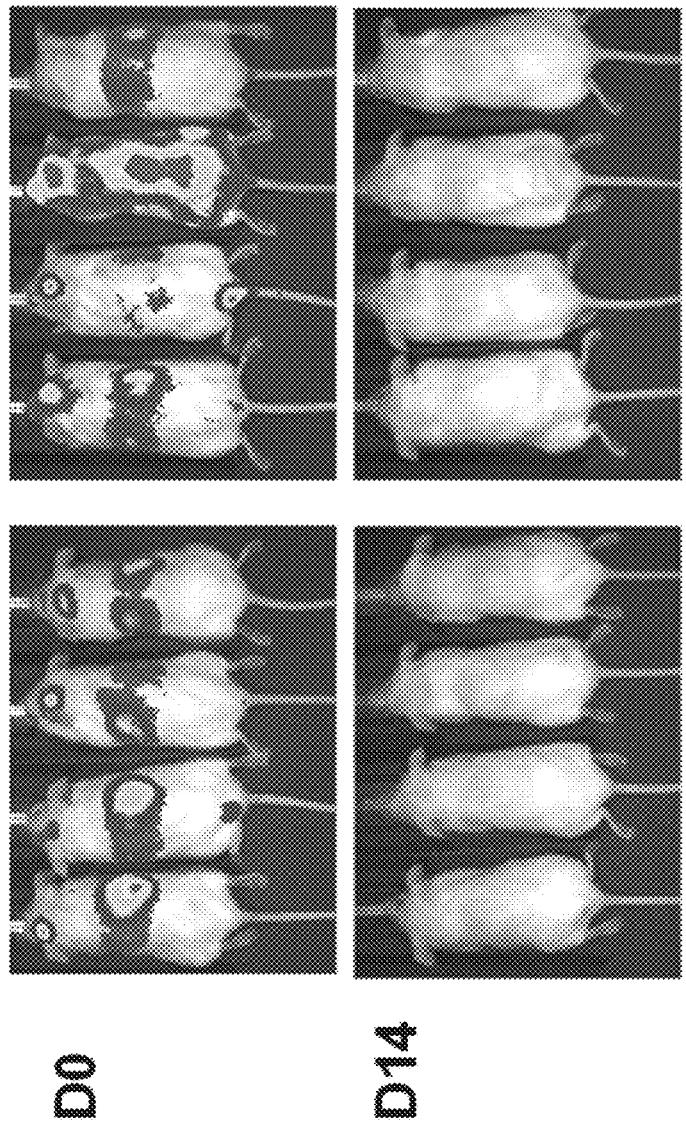

Furthermore, it was demonstrated herein that CART33 could eradicate AML while sparing CD33 KO HSPCs. NSG mice were first engrafted with control or CD33 KO HSPCs, then injected with Molm14, an AML cell line engineered to express green fluorescent protein and luciferase, followed by CART33 treatment (FIG. 11A). AML disease burden was measured by bioluminescent imaging (BLI), while human HSPCs were measured by flow cytometry of the peripheral blood. Both control and CD33 KO HSPC-engrafted mice went into AML disease remission after CART33 treatment (FIG. 11B). Tumor burden decreased in both control and CD33 KO HSPC-engrafted mice within 1-2 weeks post-CART33 treatment (FIG. 11C). CD33 KO HSPC-engrafted mice showed persistent CD14+ myeloid cells after CART33 treatment of AML in the peripheral blood (PB), spleen, and bone marrow (BM), in contrast to controls (FIG. 11D). Human progenitor cells were spared from CART33-mediated toxicity in the CD33 KO HSPC group only (FIG. 11E).

Example 3: CD33 KO Myeloid Cells are Able to Retain Normal Function

Figure 12A:
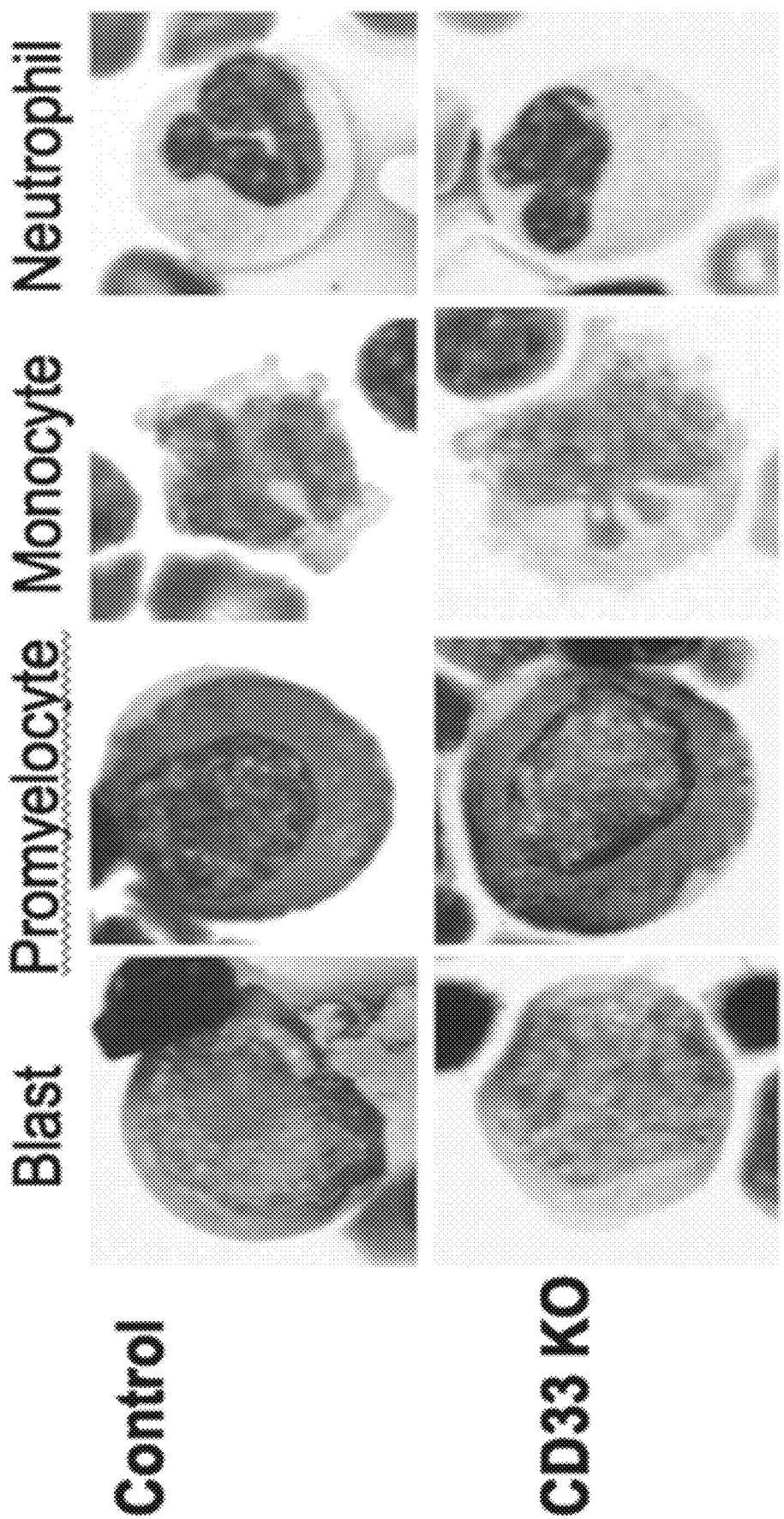
Figure 12C:
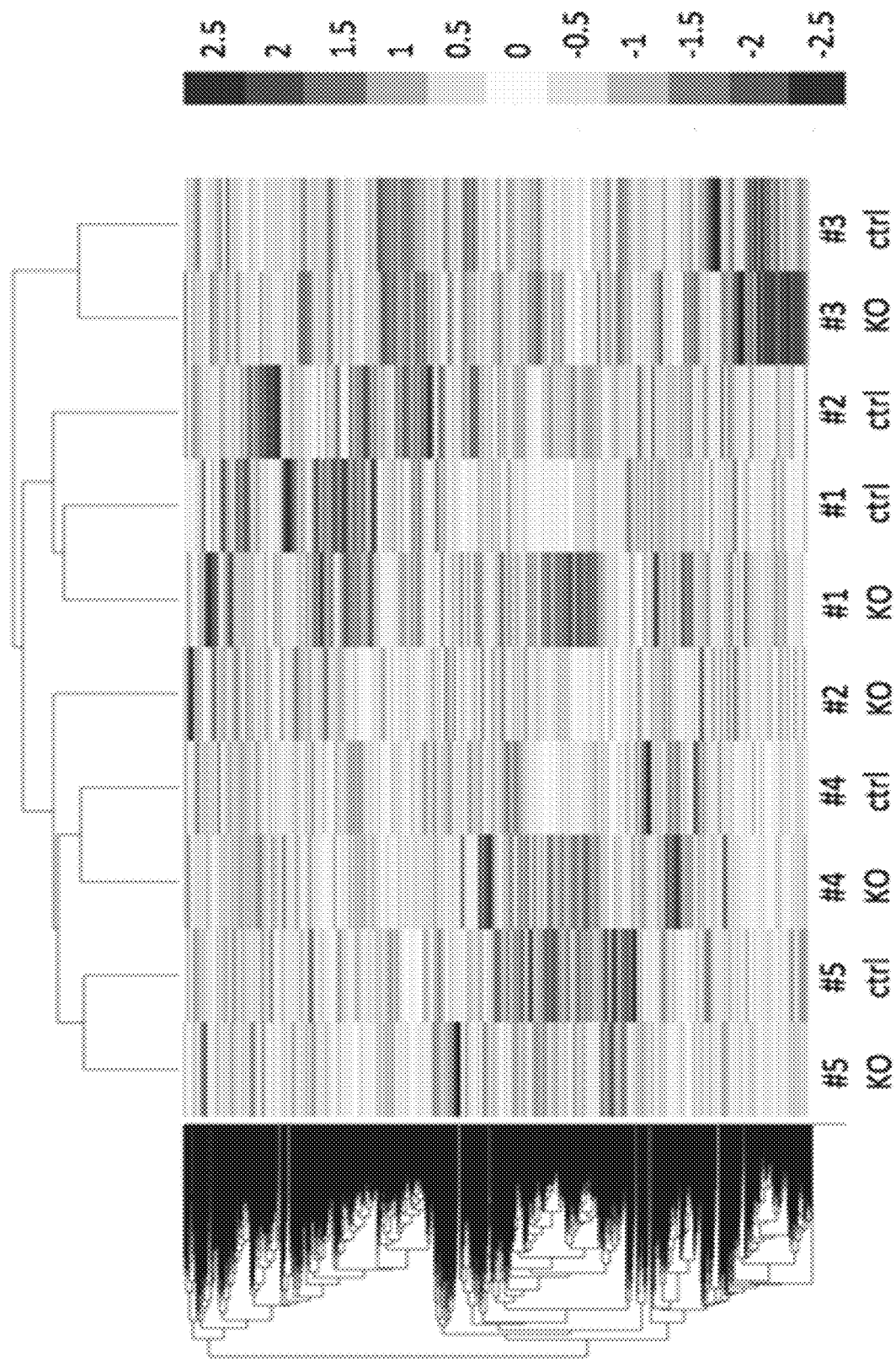
Figure 12D:
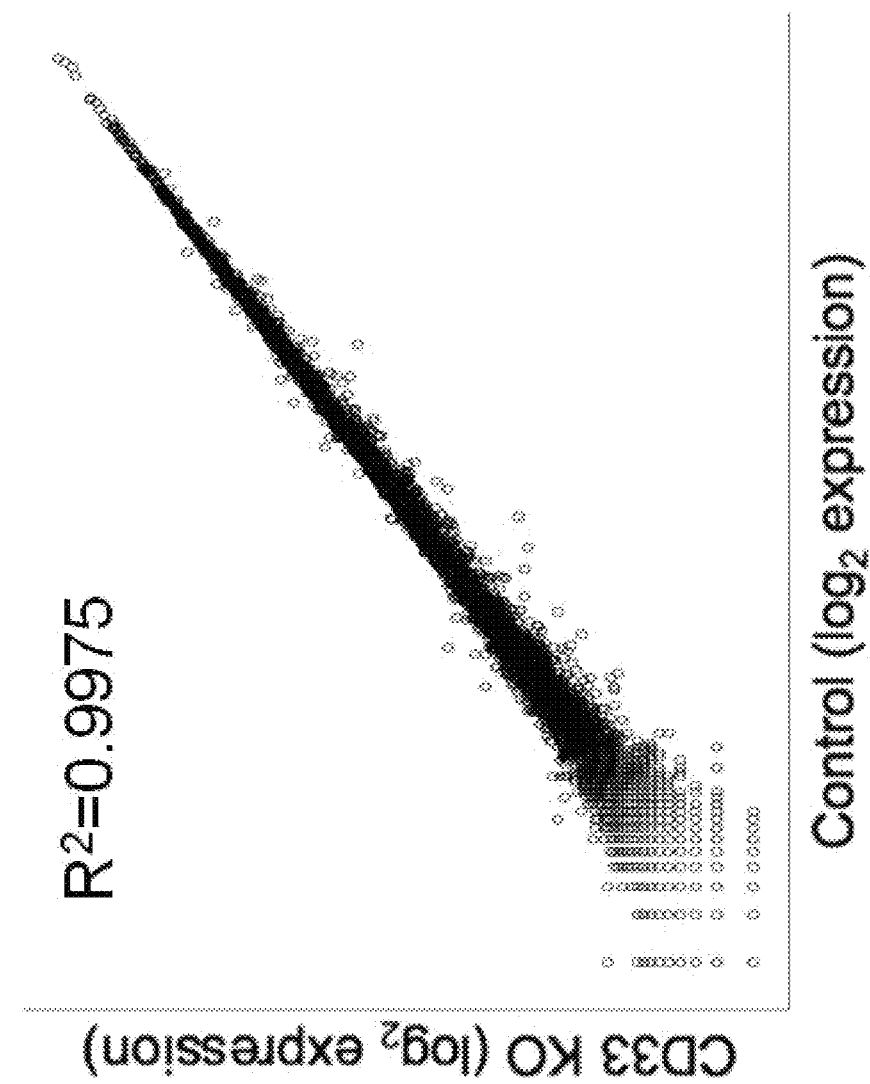
Figure 12E:
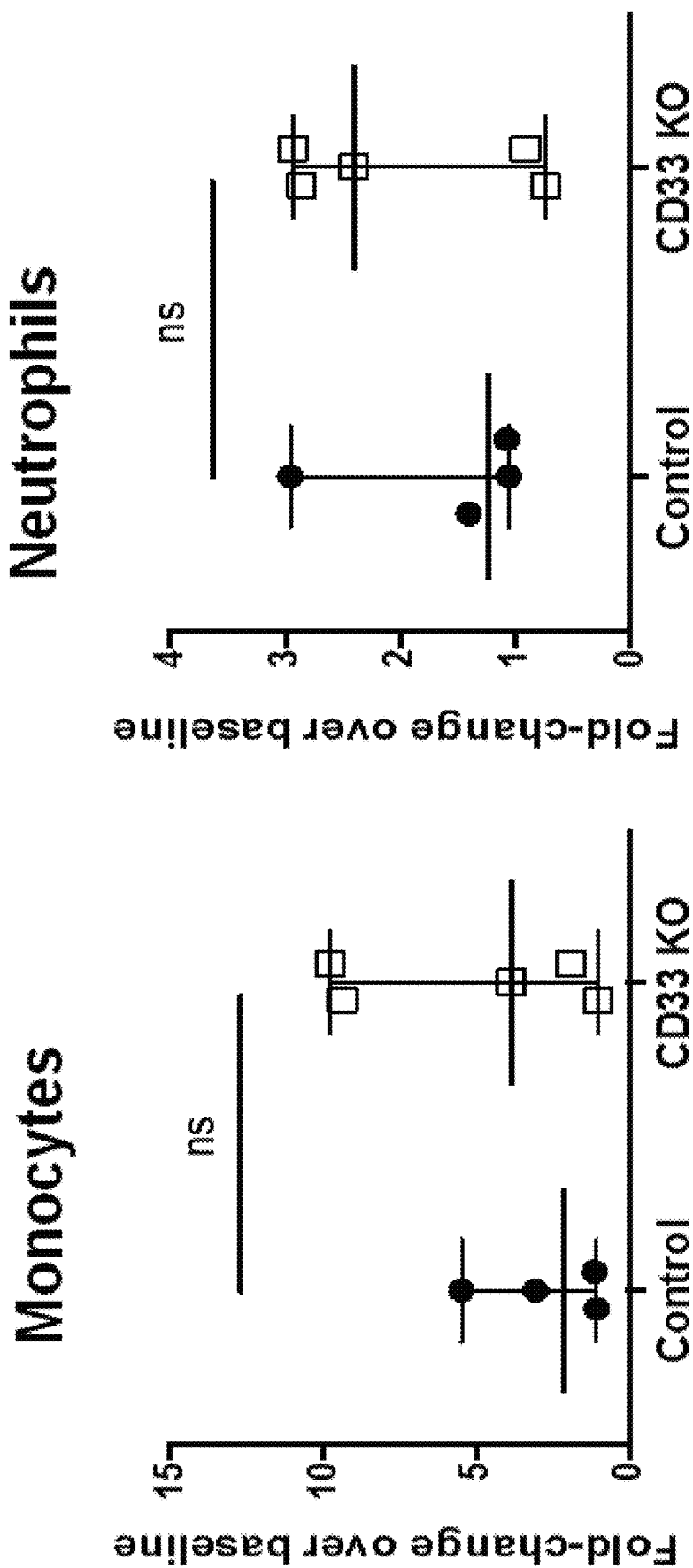
Figure 12F:
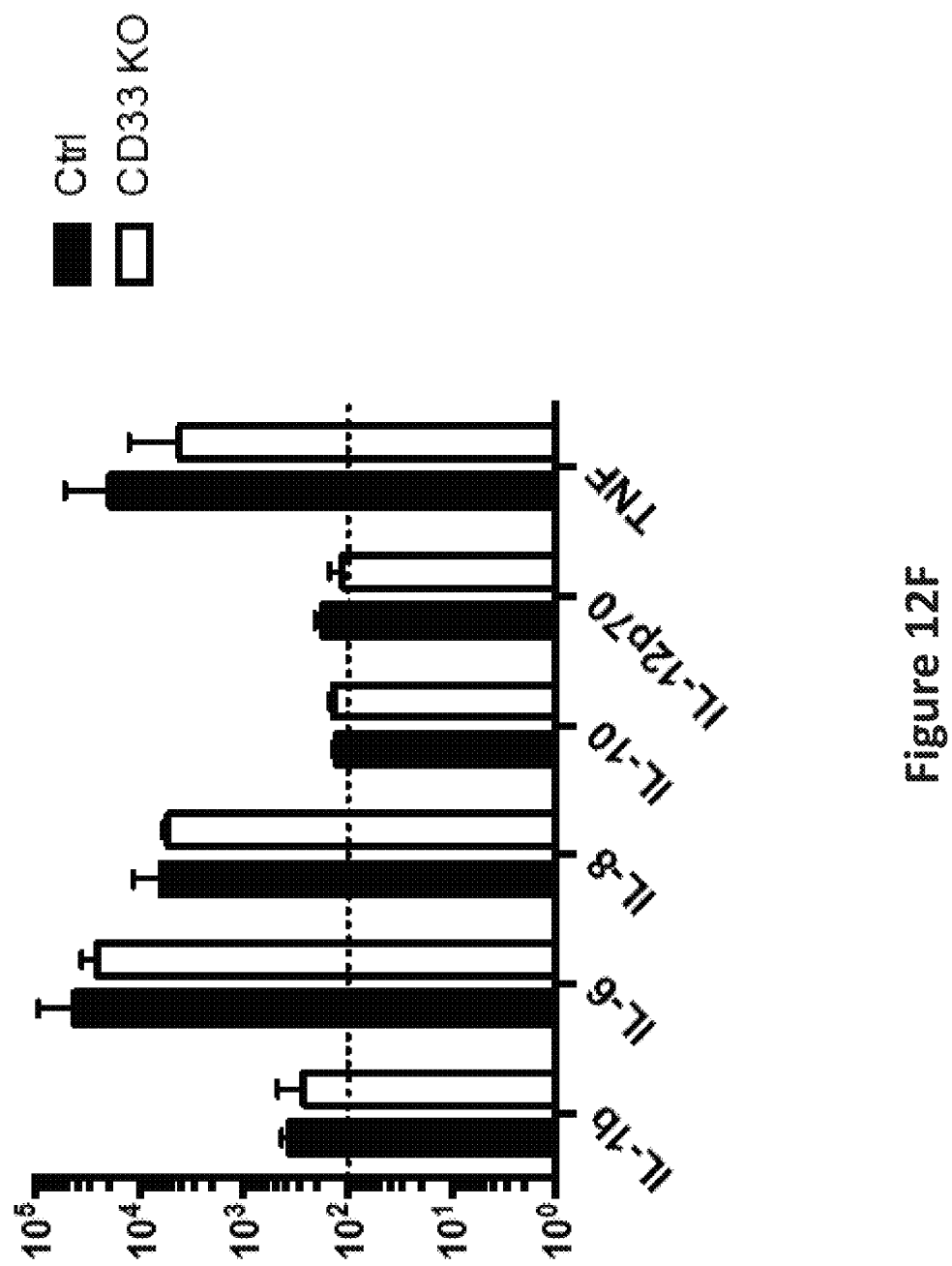

Experiments described herein demonstrated that CD33 KO HSPC progeny had no functional defects (FIGS. 12A-12F). Human cells obtained from HSPC-engrafted mouse bone marrow showed characteristic morphologic features of normal stem cell (blast), myeloid progenitor (promyelocyte), and terminal effector cells (monocytes and neutrophils) (FIG. 12A). Control or CD33 KO HSPCs were differentiated in vitro with myeloid cytokines (SCF, TPO, Flt3L, IL-6, GM-CSF, IL-3) and incubated with pHrodo green E. coli bioparticles that have green fluorescence when acidified in the phagosome (FIG. 12B). No significant differences in phagocytosis percentages was seen between control and CD33 KO HSPCs (FIG. 12B). Differentially expressed genes are depicted in FIG. 12C, with each row corresponding to genes and each column representing one sample from control (ctrl) or CD33 KO (KO); numbers indicate donor of origin. These results indicate that there is no significant perturbation of individual gene or of pathways by KO of CD33 alone. Gene expression values of control and CD33 KO samples were strongly correlated with one another (FIG. 12D). Mice were engrafted with control or CD33 KO HSPCs and injected with rhG-CSF. Absolute numbers of peripheral blood human monocytes (CD11b+ 14+) and neutrophils (CD11b+14−) were measured. There were no significant changes in cell numbers compared to baseline levels (FIG. 12E). Mice were engrafted with control or CD33 KO HSPCs and injected with lipopolysaccharide. Serum levels of human cytokines were similar between the two groups (FIG. 12F).

Figure 13A:
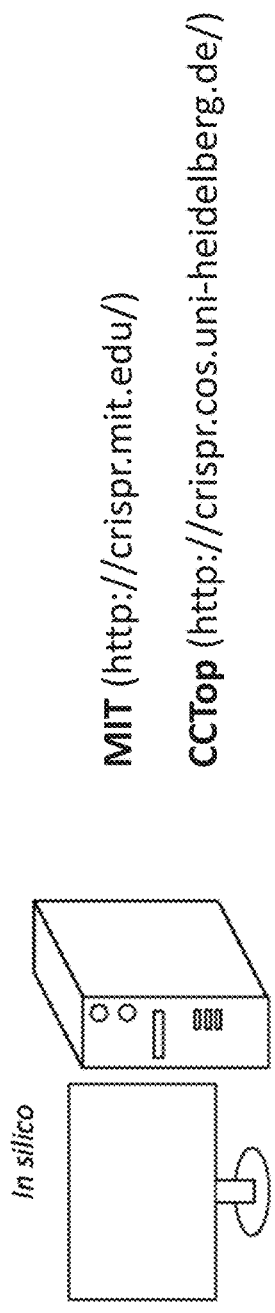
FIGS. 13A-13B are a series of images depicting off-target evaluation of CD33 KO HSPCs.
Figure 13B:
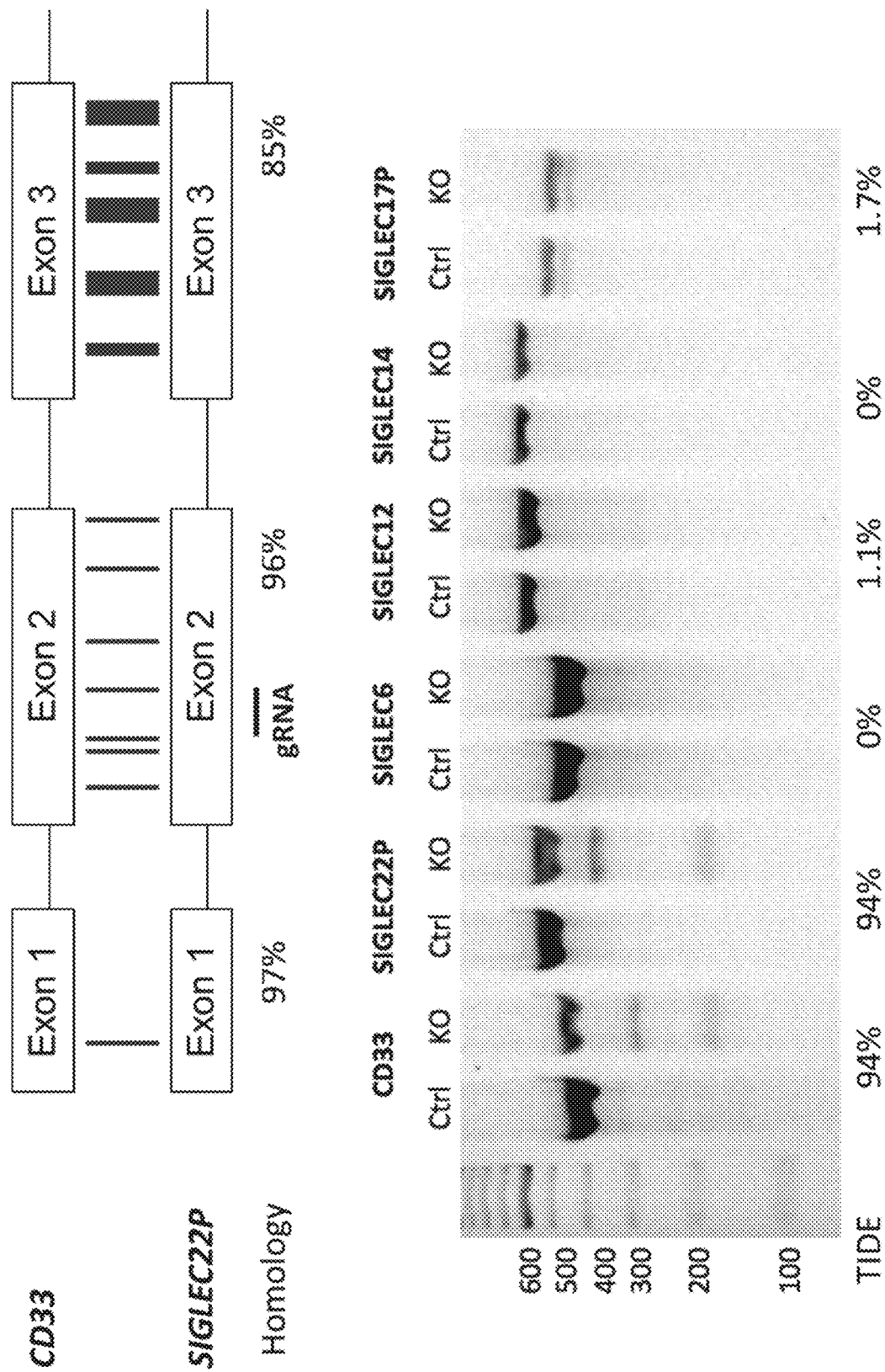
Figure 14A:
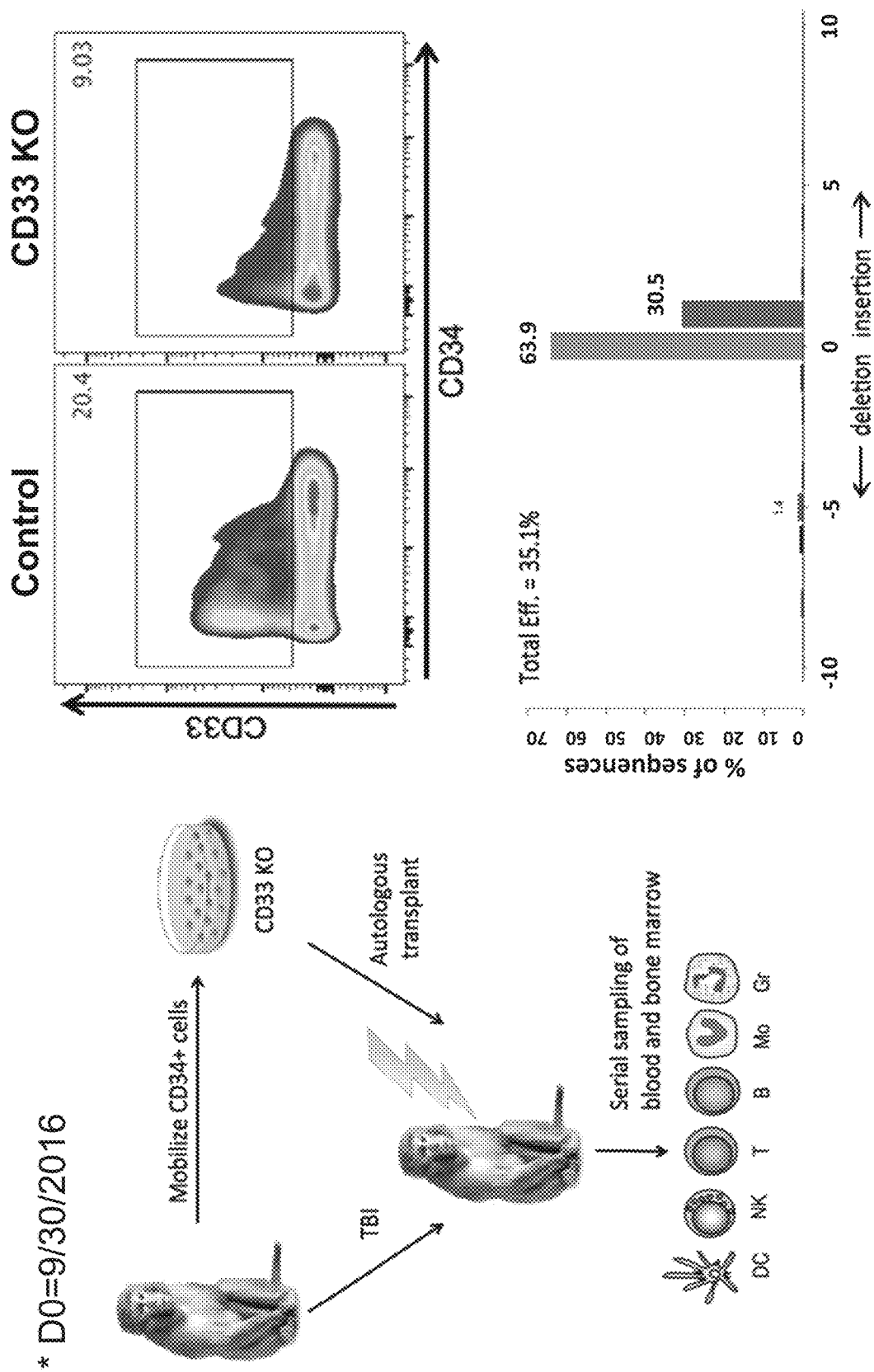
FIGS. 14A-14B are a series of plots and images depicting autologous CD33 KO stem cell transplant in Rhesus macaques.
Figure 14B:
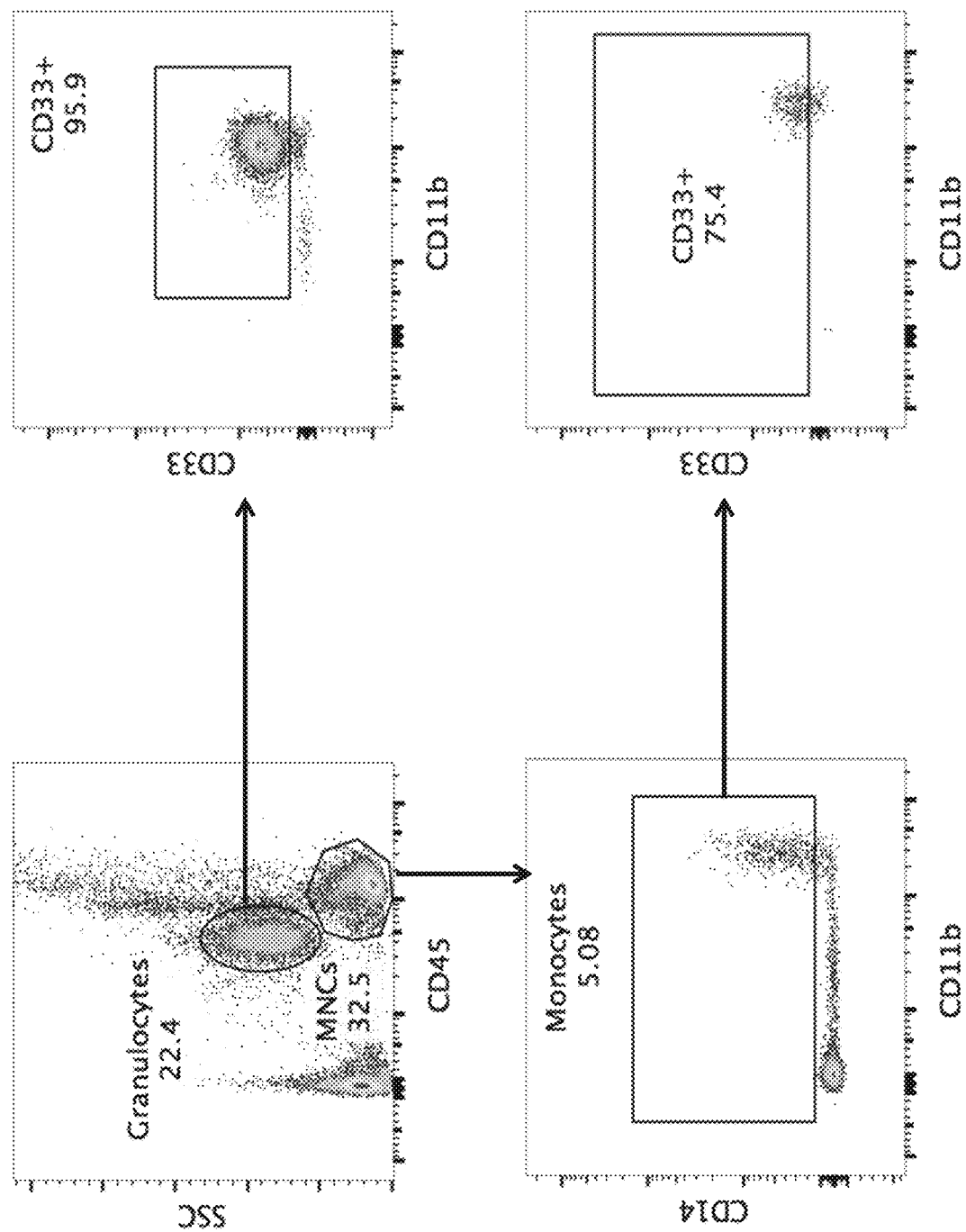

Potential off-target mutations generated by the CD33 KO protocol were investigated. Using two web tools (http://cripsr.mit.edu, http://crispr.cos.uni-heidelberg.de/), the top 12 off-target sites predicted in silico were identified (FIG. 13A). It was discovered that SIGLEC22P, a pseudogene, has a high degree of homology to the CD33 gene, with a 100% identical binding site of the CD33-targeted gRNA (FIG. 13B). Otherwise, no mutations were detected by the Surveyor mismatch assay in other SIGLEC genes, despite a high degree of on-target mutations in CD33 and SIGLEC22P (FIG. 13B).

Example 4: Autologous CD33 KO Stem Cell Transplant in Rhesus Macaques

Rhesus macaque CD34+ HSPC are mobilized using G-CSF and plerixafor, removed by apheresis, and gene edited with CRISPR/Cas9-based gene knockout of CD33. In the meantime, the monkey is conditioned with irradiation (TBI) and following that, receives a re-infusion of the edited HSPC. CD33 expression of in vitro differentiated HSPC is measured in control and KO cells. TIDE analysis of sequencing of the CD33 locus is also performed. Expression of CD33 on select sub-populations from the PB of the transplanted animal are analyzed.

The compositions and methods described herein will permit CART therapy and other potent antibody-based therapeutics e.g. BITEs to treat diseases without an identifiable cell surface marker selectively expressed on the diseased cells. The compositions and methods described herein provide a vertical advance in genetically engineered treatments.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of protecting a hematopoietic stem or progenitor cell from a chimeric antigen receptor (CAR) T cell therapy in a subject in need thereof, the method comprising administering to the subject a modified hematopoietic stem or progenitor cell, wherein the stem or progenitor cell comprises a nucleic acid that downregulates expression of an endogenous gene or a portion thereof, wherein the endogenous gene encodes a polypeptide comprising an antigen domain targeted by a CAR; and administering the CAR T cell therapy to the subject;
wherein the modified hematopoietic stem or progenitor cell differentiates into at least one blood cell type in the subject; wherein the modified hematopoietic stem or progenitor cell is capable of self-renewal after administration into the subject;
wherein the modified hematopoietic stem or progenitor cell and CAR T cells of the CAR T cell therapy are allogeneic or autologous to the subject,
wherein the subject has a myeloid disease;
wherein the nucleic acid is a CRISPR system;
wherein the CRISPR system comprises an inducible promoter; and
wherein the hematopoietic stem or progenitor cell is exposed to an agent that activates the inducible promoter in the CRISPR system.

2. The method of claim 1, wherein the CRISPR system comprises a nucleic acid encoding a Cas protein and a guide nucleic acid sequence specific for the endogenous gene.

3. The method of claim 1, wherein the CRISPR system comprises a Cas9 protein complexed with a guide nucleic acid sequence specific for the endogenous gene.

4. The method of claim 1, wherein the endogenous gene encodes a tumor antigen.

5. The method of claim 1, wherein the endogenous gene is expressed on a tumor cell targeted by the CAR.

6. The method of claim 1, wherein the endogenous gene encodes CD33, CD123, CD19 or CD22.

7. The method of claim 1, wherein the cell is obtained from a source selected from the group consisting of peripheral blood mononuclear cells, cord blood cells, bone marrow, lymph node, and spleen.

8. The method of claim 1, wherein the cell is CD34+.

9. The method of claim 1, wherein the myeloid disease is acute myeloid leukemia (AML).

* * * * *